(12) United States Patent
Avidor

(10) Patent No.: US 10,869,944 B2
(45) Date of Patent: Dec. 22, 2020

(54) SYSTEM AND METHOD FOR RELEASING EDIBLE MATERIAL

(71) Applicant: Agan Aroma & fine chemicals Ltd., Ashdod (IL)

(72) Inventor: Yoav Avidor, Tel-Aviv (IL)

(73) Assignee: Agan Aroma & fine chemicals Ltd., Ashdod (IL)

( * ) Notice: Subject to any disclaimer, the term of this patent is extended or adjusted under 35 U.S.C. 154(b) by 84 days.

(21) Appl. No.: 15/536,201

(22) PCT Filed: Dec. 17, 2015

(86) PCT No.: PCT/IL2015/051225
§ 371 (c)(1),
(2) Date: Jun. 15, 2017

(87) PCT Pub. No.: WO2016/098115
PCT Pub. Date: Jun. 23, 2016

(65) Prior Publication Data
US 2017/0360979 A1 Dec. 21, 2017

Related U.S. Application Data

(60) Provisional application No. 62/092,875, filed on Dec. 17, 2014.

(51) Int. Cl.
*B65G 59/00* (2006.01)
*A47F 1/04* (2006.01)
(Continued)

(52) U.S. Cl.
CPC ............... *A61L 9/035* (2013.01); *A23L 27/00* (2016.08); *A61L 9/012* (2013.01); *A61L 9/122* (2013.01);
(Continued)

(58) Field of Classification Search
CPC .......... G07F 9/00; G07F 11/002; G07F 11/00; F25D 31/006
(Continued)

(56) References Cited

U.S. PATENT DOCUMENTS 2,686,944 A 8/1954 Gubelin
5,898,475 A 4/1999 Martin
(Continued)

FOREIGN PATENT DOCUMENTS

BR PI 201002877-3 6/2012
BR 102013010090-0 11/2015
(Continued)

OTHER PUBLICATIONS

Official Action dated Dec. 31, 2018 From the US Patent and Trademark Office Re. U.S. Appl. No. 15/536,149. (19 pages).
(Continued)

*Primary Examiner* — Monzer R Chorbaji

(57) ABSTRACT

A system for releasing edible material is disclosed. The system comprises: a plurality of compartments adapted to receive a respective plurality of capsules, each capsule containing therein an edible material; a dispenser system configured for dispensing into an environment a fluid obtained from at least one edible material; and a controller configured for receiving data pertaining to a selection of at least two of the compartments and for signaling the dispenser system to dispense fluids obtained from edible materials contained in capsules of the selected compartments.

23 Claims, 2 Drawing Sheets

(51) Int. Cl.
- *A61L 9/03* (2006.01)
- *A23L 27/00* (2016.01)
- *A61L 9/012* (2006.01)
- *A61L 9/12* (2006.01)
- *A61L 9/14* (2006.01)

(52) U.S. Cl.
CPC ............... *A61L 9/125* (2013.01); *A61L 9/14* (2013.01); *A61L 2209/11* (2013.01); *A61L 2209/132* (2013.01)

(58) Field of Classification Search
USPC ..... 422/1, 40; 99/450.1; 221/67–68, 92, 303
See application file for complete search history.

(56) References Cited

U.S. PATENT DOCUMENTS

| | | | |
|---|---|---|---|
| 5,924,597 | A | 7/1999 | Lynn |
| 6,241,944 | B1 | 6/2001 | Budman |
| 6,282,458 | B1 * | 8/2001 | Murayama ............... A61L 9/122 422/108 |
| 8,170,405 | B2 | 5/2012 | Harris |
| 8,622,241 | B2 | 1/2014 | Geboers et al. |
| 2003/0164557 | A1 | 9/2003 | Chung et al. |
| 2004/0007787 | A1 | 1/2004 | Kvietok et al. |
| 2004/0175287 | A1 | 9/2004 | Nakatsu et al. |
| 2004/0237793 | A1 | 12/2004 | Zurcher et al. |
| 2006/0153731 | A1 | 7/2006 | Brown et al. |
| 2007/0012718 | A1 | 1/2007 | Schramm et al. |
| 2007/0138326 | A1 | 6/2007 | Hu |
| 2010/0129268 | A1 * | 5/2010 | Andersen ............... G06Q 99/00 422/124 |
| 2014/0001286 | A1 | 1/2014 | Scott et al. |
| 2017/0360981 | A1 | 12/2017 | Avidor |

FOREIGN PATENT DOCUMENTS

| | | |
|---|---|---|
| CN | 101522227 | 9/2009 |
| CN | 102573928 | 7/2012 |
| EP | 0831384 | 3/1998 |
| JP | 10-085315 | 4/1998 |
| JP | 10-146385 | 6/1998 |
| JP | 3556235 | 8/2004 |
| JP | 2005-507294 | 3/2005 |
| JP | 2005-224504 | 8/2005 |
| JP | 2005-528133 | 9/2005 |
| JP | 2006-523929 | 10/2006 |
| JP | 2009-189410 | 8/2009 |
| JP | 2013-146411 | 8/2013 |
| JP | 2014-500472 | 1/2014 |
| WO | WO 03/039309 | 5/2003 |
| WO | WO 03/056493 | 7/2003 |
| WO | WO 2012/027808 | 3/2012 |
| WO | WO 2012/078973 | 6/2012 |
| WO | WO 2014/176291 | 10/2014 |
| WO | WO 2016/098114 | 6/2016 |
| WO | WO 2016/098115 | 6/2016 |

OTHER PUBLICATIONS

International Preliminary Report on Patentability dated Jun. 29, 2017 From the International Bureau of WIPO Re. Application No. PCT/IL2015/051224. (7 Pages).
International Preliminary Report on Patentability dated Jun. 29, 2017 From the International Bureau of WIPO Re. Application No. PCT/IL2015/051225. (7 Pages).
International Search Report and the Written Opinion dated Mar. 30, 2016 From the International Searching Authority Re. Application No. PCT/IL2015/051224.
International Search Report and the Written Opinion dated Mar. 30, 2016 From the International Searching Authority Re. Application No. PCT/IL2015/051225.
Notification of Office Action and Search Report dated Sep. 11, 2018 From the State Intellectual Property Office of the People's Republic of China Re. Application No. 201580068751.X. (9 Pages).
Notification of Office Action and Search Report dated Sep. 11, 2018 From the State Intellectual Property Office of the People's Republic of China Re. Application No. 201580068758.1. (8 Pages).
Supplementary Partial European Search Report and the Provisional Opinion dated Sep. 5, 2018 From the European Patent Office Re. Application No. 15869474.5. (12 Pages).
Translation dated Oct. 4, 2018 of Notification of Office Action dated Sep. 11, 2018 From the State Intellectual Property Office of the People's Republic of China Re. Application No. 201580068751.X. (7 Pages).
Translation Dated Oct. 4, 2018 of Notification of Office Action dated Sep. 11, 2018 From the State Intellectual Property Office of the People's Republic of China Re. Application No. 201580068758.1. (6 Pages).
Supplementary European Search Report and the European Search Opinion dated Oct. 12, 2018 From the European Patent Office Re. Application No. 15869473.7. (8 Pages).
Notification of Office Action and Search Report dated Jun. 13, 2019 From the State Intellectual Property Office of the People's Republic of China Re. Application No. 201580068758.1 and Its Translation of the Notification of Office Action Into English.(10 Pages).
Supplementary European Search Report and the European Search Opinion dated Aug. 16, 2019 From the European Patent Office Re. Application No. 15869474.5. (12 Pages).
Office Action dated Jun. 13, 2019 From the State Intellectual Property Office of the People's Republic of China Re. Application No. 201580068751 and Its Translation of the Notification of Office Action Into English. (15 Pages).
Notice of Reasons for Rejection dated Oct. 1, 2019 From the Japan Patent Office Re. Application No. 2017-531760 and Its Translation Into English. (10 Pages).
Notice of Reasons for Rejection dated Oct. 1, 2019 From the Japan Patent Office Re. Application No. 2017-531768. (5 Pages).
Translation Dated Oct. 16, 2019 of Notice of Reasons for Rejection dated Oct. 1, 2019 From the Japan Patent Office Re. Application No. 2017-531768. (11 Pages).
Examination Report Under Sections 12 & 13 of the Patents Act, 1970 and the Patents Rules, 2003 dated Feb. 12, 2020 From the Government of India, Intellectual Property India, Patents, Designs, Trade Marks, Geographical Indications, The Patent Office Re. Application No. 201727024529. (6 Pages).
Examination Report dated May 5, 2020 From the Australian Government, IP Australia Re. Application No. 2015365324. (6 Pages).
Examination Report dated Apr. 23, 2020 From the Australian Government, IP Australia Re. Application No. 2015365323. (4 Pages).
Search Report and Explanation dated Mar. 25, 2020 From the Servico Publico Federal, Ministerio da Economia, Instituto Nacional da Propriedade Industrial do Brasil Re. Application No. BR112017012645-1 and Its Summary in English. (5 Pages).
Search Report and Explanation dated Mar. 25, 2020 From the Servico Publico Federal, Ministerio da Economia, Instituto Nacional da Propriedade Industrial do Brasil Re. Application No. BR112017012649-4 and Its Summary in English. (5 Pages).
Examination Report Under Sections 12 & 13 of the Patents Act, 1970 and the Patents Rules, 2003 Dated Sep. 30, 2020 From the Government of India, Intellectual Property India, Patents, Designs, Trade Marks, Geographical Indications Re. Application No. 201727024470. (6 Pages).
Notice of Reasons for Rejection Dated Sep. 1, 2020 From the Japan Patent Office Re. Application No. 2017-531760 and Its Translation Into English. (9 Pages).
Office Action Dated Sep. 14, 2020 From the Israel Patent Office Re. Application No. 252925 and Its Translation Into English. (12 Pages).
Office Action Dated Sep. 15, 2020 From the Israel Patent Office Re. Application No. 252926 and Its Translation Into English. (13 Pages).

* cited by examiner

US 10,869,944 B2

SYSTEM AND METHOD FOR RELEASING EDIBLE MATERIAL

RELATED APPLICATIONS

This application is a National Phase of PCT Patent Application No. PCT/IL2015/051225 having International filing date of Dec. 17, 2015, which claims the benefit of priority under 35 USC § 119(e) of U.S. Provisional Patent Application No. 62/092,875 filed on Dec. 17, 2014. The contents of the above applications are all incorporated by reference as if fully set forth herein in their entirety.

FIELD AND BACKGROUND OF THE INVENTION

The present invention, in some embodiments thereof, relates to the release of a fluid and, more particularly, but not exclusively, to a system and method for releasing edible material.

In any place where people gather there will be various odors, fragrances and the like. It is common for homeowners and businesses to oftentimes struggle to maintain pleasant smelling environments. Many odors from such various things as cooking, personal hygiene products, the presence of pets, and cigarette smoke can be present in a home or business. Odors of these types are often difficult to combat.

Aroma emitting devices are well known and are commonly used in homes and commercial establishments to provide a pleasant atmosphere for people in given areas. Such devices passively or actively transmit aromas to the general surroundings.

Examples of passive devices include air wicks, scented gel-packs, and aromatic sticks resting in a bottle of aromatic liquid and protruding out of the bottle so that the liquid is absorbed and drawn upward through the stick where upon, the liquid evaporates from the surface of the stick. One type of active aromatic device is plugged into an electrical power outlet, whereupon, a small heating element heats an aromatic liquid containing member thus causing the liquid to evaporate and escape into the adjacent surroundings. Another example of an active aromatic device is powered by battery or wall outlet and sprays an aromatic mist periodically into a room.

Aromatic devices are commonly used by individuals who enjoy various selected scents. Further, the use of such aromatic devices has been found to improve or enhance the general demeanor of individuals in a particular surrounding. Certain scents have been found to cause desirable mood changes in people in general.

SUMMARY OF THE INVENTION

According to an aspect of some embodiments of the present invention there is provided a system for releasing edible material. The system comprises: a plurality of compartments adapted to receive a respective plurality of capsules, each capsule containing therein an edible material; a dispenser system configured for dispensing into an environment a fluid obtained from at least one edible material; and a controller configured for receiving data pertaining to a selection of at least two of the compartments and for signaling the dispenser system to dispense fluids obtained from edible materials contained in capsules of the selected compartments.

According to some embodiments of the invention each of at least two of the plurality of capsules contains therein a different edible material.

According to some embodiments of the invention each of at least two of the plurality of capsules contains the same edible material but at a different concentration.

According to some embodiments of the invention the dispenser system comprises a plurality of dispensing elements and wherein the controller signals each dispensing element to dispense a fluid obtained from an edible material contained in a different capsule.

According to some embodiments of the invention the dispenser system comprises at least one fluid channel forming fluid communication between a respective compartment and the environment, wherein the controller is configured for opening and blocking the at least one fluid channel, thereby to establish or prevent the fluid communication.

According to some embodiments of the invention the system comprises a mixing chamber, wherein the dispenser system comprises at least one fluid channel forming fluid communication between a respective compartment and the mixing chamber, and wherein the controller is configured for opening and blocking the at least one fluid channel, thereby to establish or prevent the fluid communication.

According to some embodiments of the invention the controller is configured for receiving data pertaining to a mixing ratio, and to control amounts of the fluids responsively to the mixing ratio.

According to some embodiments of the invention the system comprises a weight measuring device constituted to measure a weight of each capsule separately.

According to some embodiments of the invention the system comprising a user interface configured for at least one of (i) activating the controller and/or the dispenser system, (ii) deactivating the controller and/or the dispenser system, and (iii) entering the selection data.

According to some embodiments of the invention the invention the system comprises a weight measuring device constituted to measure a weight of each capsule separately, wherein the controller is configured for receiving weight data from the weight measuring device and to control the amounts based on the weight data.

According to some embodiments of the invention the invention the system comprises a user interface configured for entering the mixing ratio.

According to some embodiments of the invention the invention the system is encapsulated in an encapsulation, wherein the user interface is mounted on the encapsulation.

According to some embodiments of the invention the invention the system comprises a communication system configured for communicating with a remote user interface.

According to some embodiments of the invention the invention the dispenser system is configured for heating the edible material to form the fluid.

According to some embodiments of the invention the heating is by a flame.

According to some embodiments of the invention the heating is by a resistive heater.

According to some embodiments of the invention the invention the dispenser system is configured to apply ultrasound waves to the edible material thereby to dispense the fluid.

According to some embodiments of the invention the invention the dispenser system is configured to apply a stream of gas to the edible material thereby to dispense the fluid.

According to some embodiments of the invention the invention the dispenser system comprises an atomizer.

According to some embodiments of the invention the invention the dispenser system comprises a humidifier.

According to some embodiments of the invention the invention the dispenser system comprises a blower or a fan.

According to some embodiments of the invention the invention at least one of the capsules contains the edible material in a solid state as room temperature.

According to some embodiments of the invention the invention at least one of the capsules contains the edible material in a liquid state as room temperature.

According to an aspect of some embodiments of the present invention there is provided a method of releasing an edible material into an environment, comprising loading into a system for releasing an edible material a plurality of capsules, each containing therein an edible material, and activating the system to dispense a fluid obtained from an edible material contained in at least one of the capsules, wherein the system for releasing edible material is as delineated above and optionally as further detailed below.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
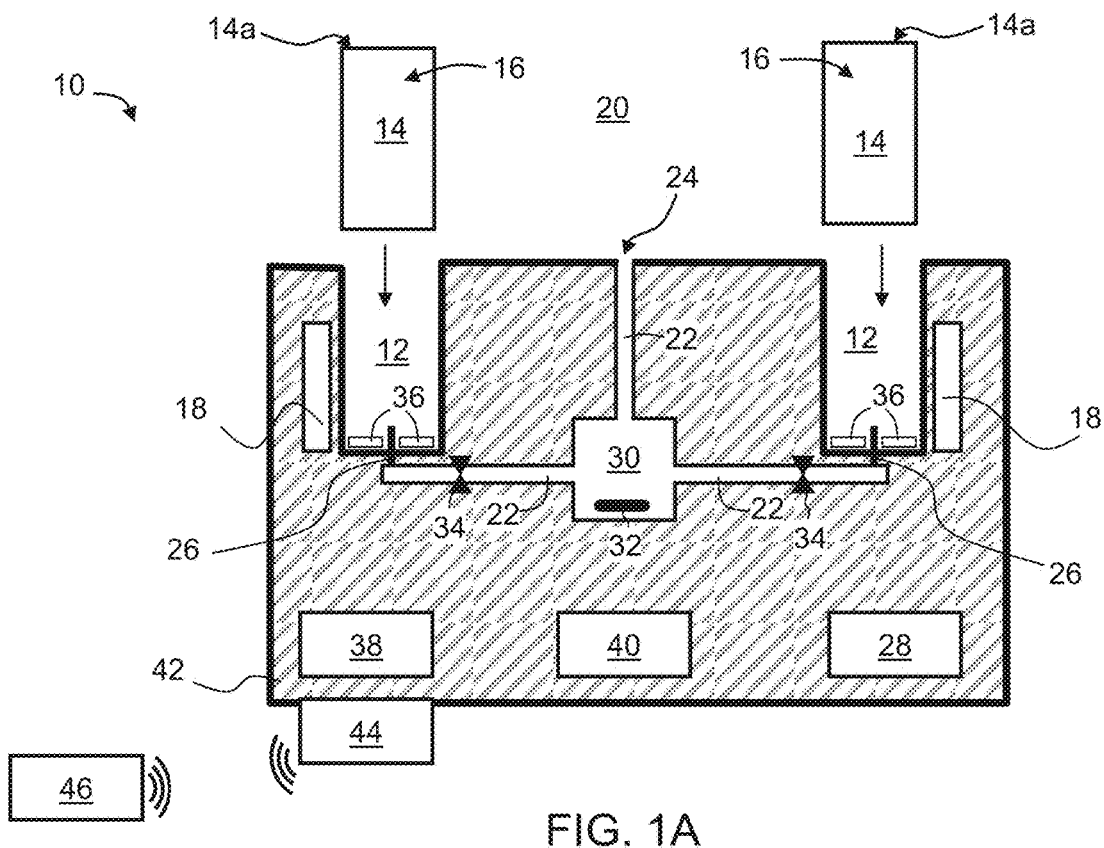
FIG. 1A is a schematic illustration of a system for releasing an edible material into the environment, according to some embodiments of the present invention.

The present invention, in some embodiments thereof, relates to the release of a fluid to the environment and, more particularly, but not exclusively, to a system and method for releasing an edible material.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
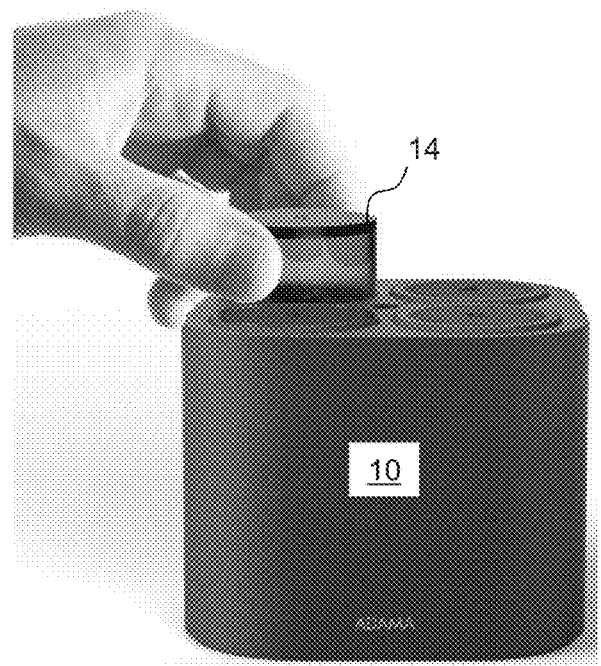
FIG. 1B is an image of a system for releasing an edible material into the environment, according to some embodiments of the present invention.

Referring now to the drawings, FIGS. 1A and 1B are a schematic illustration (FIG. 1A) and an image (FIG. 1B) of a system 10 for releasing an edible material into the environment, according to some embodiments of the present invention. System 10 is optionally and preferably electrically operated either by means of batteries and/or by connecting the system to a DC or AC power source.

System 10 preferably comprises one or more compartments 12, preferably a plurality of compartments 12. FIG. 1A shows two compartments and FIG. 1B shows four compartments, but system 10 can include an number of compartments, preferably four or more.

Each of the compartments is adapted to receive a capsule 14 containing therein an edible material 16.

While FIGS. 1A and 1B show embodiments in which the capsules are received by the compartments from above, this need not necessarily be the case, since, for some applications, it may be desired to construct the compartments to receive the capsules from the side or from below. The present embodiments also contemplate configurations in which one or more compartments receive the capsules from above, and one or more compartments receive the capsules from the side.

As used herein, the term "edible material" refers a substance intended and suitable for oral contact or consumption by eating.

The edible material can, in some embodiments, comprise one or more substances having a CAS No. selected from the group consisting of the CAS Nos. listed in Appendix A.

System 10 can be used for modifying a taste of a food product, or for providing a taste-modifying substance that can be used for modifying a taste of a food product.

The edible material can be in a solid state or in a liquid state at room temperature. Typically, the edible material is in a liquid state at room temperature.

In some embodiments, two or more of the capsules, optionally and preferably all the capsules, contain different edible materials, in some embodiments two or more of the capsules contain the same edible material, and in some embodiments two or more of the capsules contain same edible material but at a different concentration.

In some embodiments of the present invention system 10 comprises a dispenser system 18 configured for dispensing into the environment 20 a fluid obtained from at least one edible material in the capsules. Dispenser system 18 is shown in FIG. 1A as separate dispensing elements, one for each compartment, but this need not necessarily be the case, since, for some applications, system 18 can be provided, for example, as a single unit.

Dispenser system 18 can employ any technology that allows obtaining a fluid from the edible material in the capsules.

In some embodiments of the present invention system 18 employs heating. In these embodiments, the heat provides the edible material with thermal energy that breaks up or excites the bonds of taste modifiers and allows them to flow. The heat can be applied by convection, radiation or conduction. In some embodiments of the present invention system 18 comprises a heat source, e.g., a flame based heat source, or, more preferably, a resistive heat source, e.g., in the form of a filament resistor, a power resistor or a coil. In some embodiments of the present invention system 18 comprises a light source that directs radiation onto the edible material at a wavelength that heats the material. For example, the light source can apply infrared radiation.

In some embodiments of the present invention system 18 applies ultrasound waves to the edible material. The ultrasound wave provides the edible material with mechanical energy (e.g., vibration) that breaks up or excites the bonds of taste modifiers and allows them to flow.

In some embodiments of the present invention system 18 atomizes the edible material.

As used herein "atomizing" and "atomization" refer to the conversion of a liquid medium into a spray or mist (i.e., a collection of droplets). Atomization can occur by passing a liquid medium through a nozzle or aperture. The terms "atomizing" and "atomization" do not necessarily mean that the spray or mist or the particles therefrom are reduced to atomic sizes. Atomizing a liquid medium can be achieved by use of an atomizer. Atomizers are known and are commercially available, such as from TSI, Inc. of Shoreview Minn., USA.

System 18 can release the fluid directly into the environment, for example, through a surface 14a of capsule 14. In these embodiments, upper surface 14a is preferably exposed to the environment and is made permeable to the fluid that is formed from the edible material, but not to the edible material itself. These embodiments are useful when the edible material is in solid form or when the molecules of the obtained fluid are substantially smaller than the molecules of the edible material.

Alternatively, system 18 can comprise one or more fluid channel 22 into which the fluid is released. One or more of the fluid channels can have an opening 24 to the environment 20, so that fluid obtained from the edible material in a particular capsule, or fluids obtained from edible materials in several capsules can be released through opening 24.

The environment 20 can be embodied as an external container that collects the released edible material, or a food product on which the edible material is applied.

In some embodiments of the present invention compartment 12 includes a piercing member 26 (such a nozzle or a hollow needle) that pierces the capsule and establishes fluid communication with fluid channel 22. Piercing member 26 can be positioned to protrude inwardly from the base of compartment 12, as illustrated in FIG. 1A. Alternatively, piercing member 26 can protrude inwardly from the side walls of compartment 12. When the compartment receives the capsule not from above, the piercing member can protrude inwardly from a top surface (not shown) of the compartment. Also contemplated are embodiments in which several piercing members are employed, for example, one or more at the base of the compartment and/or one or more at the side walls of the compartment.

The piercing member can be static in which case the capsule is pierced once fitted into the respective compartment. For example, when a static piercing member protrudes outwardly from the base of the comportment, the operator can conveniently press on the upper surface 14a of the capsule to effect the piercing. The piercing member can alternatively be movable perpendicularly to the inner surface (base, side wall, upper surface) of the compartment from which the piercing is effected. Piercing of the capsule is effected when the piercing member moves inwardly. Once the capsule is pierced, the piercing member can be retracted backwardly. Inward and backward motion of the piercing member can be established by a controller as further detailed hereinbelow, or manually, for example, by means of a lever or a button (not shown).

Once the capsule is pierced, fluid obtained from the edible material flows through the thus formed piercing from the capsule into the channel 22 and then from channel 22 into the environment 20. Alternatively, the fluid can flow from the capsules into a mixing chamber 30 and then from the mixing chamber into the environment. The flow from the mixing chamber 30 to the environment can be achieved by virtue of an increased gas pressure in chamber 30 relative to the environment, or by means of a fan or a blower 32 operated by dispenser system 18.

In various exemplary embodiments of the invention system 10 comprises a controller 28 configured for receiving data pertaining to a selection of two or more of the compartments and for signaling dispenser system 18 to dispense fluids obtained from edible materials contained in the capsules of selected compartments. In various exemplary embodiments of the invention controller causes the release of fluids obtained from two or more capsules simultaneously. This can be achieved by simultaneous activation of different dispensing elements, or by allowing fluids to mix at mixing chamber prior to their release.

There are several advantages for the ability to release more than one fluid. For example, one selected compartment can contain a capsule having a taste modifier and another compartment can contain a capsule having a taste neutralizing material. Depending on the taste modifier and the taste neutralizing material can be selected. Another advantage is that selecting more than one compartment can allow the operator to cause system 10 to release material combinations according to the desire of the user.

When dispenser system 18 comprises a plurality of dispensing elements, controller 28 optionally and preferably signals each of the dispensing elements independently.

When system 10 comprises mixing chamber 30, controller 28 optionally and preferably opens, at least temporarily, fluid channels from the selected compartments to mixing chamber 30. This can be achieved by providing one or more of channels 22 with valves 34 that are controlled by controller 28.

When system 10 comprises movable piercing members 26, controller 28 can also control the operation of piercing members 26. For example, during the loading of a capsule into one of the compartments, the piercing member can be in a backward state (namely not protruding inwardly with respect to the interior of the compartment).

Once the data pertaining to the selection of two or more compartments is received by controller 28 and system 10 is in operation, controller 28 can signal only the piercing members of the selected compartment to pierce the respective capsule, thereby ensuring that only fluids that are obtained from the capsules in the selected compartments are eventually released into the environment.

Alternatively, all the capsules can be pierced and the control over the release of a particular fluid to the environment can be achieved by means of controlling valves 34 and/or whether or not the respective dispensing element is operative.

In some embodiments of the present invention controller 28 also receives data pertaining to a mixing ratio, and controls the amounts of fluids obtained from different edible materials responsively to the received mixing ratio. The control over the amount of a particular fluid that is eventually released into the environment (either directly or via fluid channel 22 or via mixing chamber 30, can be achieved for example, by executing a timing protocol, wherein the time during which a particular fluid is allowed to flow is selected based on the mixing ratio. For example, when it is desired to mix an edible material from a first capsule and an edible material from a second capsule at a ratio of 2:1, the fluid from the first capsule can be allowed to flow during a certain time interval Δt and the fluid from the second capsule can be allowed to flow during half the interval Δt.

In some embodiments of the present invention system 10 comprises a weight measuring device 36 constituted to measure a weight of each capsule separately. This embodiment is useful for determining the amount of edible material that remains in each capsule, for example, for the purpose of providing notification to the operator.

Optionally, system 10 comprises a display 38, and controller 28 receives weight data from device 36 and controls display 38 to present information to the operator. Information may include information pertinent to battery life, duration or other suitable indicator associated with capsule replacement, mixing ratio, taste intensity and the like. It is appreciated that the list of information provided above is not exhaustive but, rather is representative of various parameters that a user may find valuable in assessing and/or maintaining a desired operation of system 10. Display 38 may be an LCD or a LED display or other suitable display capable of displaying one or more parameters associated with the operation of the device.

The weight data can also be used by controller 28 for maintaining the mixing ration between fluids. Based on the change in the weight of each capsule, the controller can predetermine the amount of the fluid that has been obtained from the respective capsule, and can therefore control the flow of the respective fluids so as to maintain the ratio.

System 10 preferably comprises a user interface 40. The user interface may include buttons, which are activated by pressing, and may take different shapes depending on each button's particular function. The user interface may also include LEDs to indicate operational status information such as low battery or low level of edible material in a particular capsule. The user interface may also include a touch screen or a keyboard. The user interface may also be a voice activated interface.

The user interface can allow the operator to program the release of fluids in a manner preferred by the operator. For example, the user interface may allow the user to program the speed of dispensing, e.g., by choosing the number of days of dispensing, the amount of each dispense activity, the hours of the day associated with dispensing, the duration of the dispensing, etc. It is understood that selecting a shorter duration at a greater rate of dispensing and selecting longer duration at a slower rate of dispensing can generate similar duration and intensity profiles. The user interface can also allow the user to program other features of system 10 such as, but not limited to, daylight settings, on and off hours, and the like. In various exemplary embodiments of the invention the user interface allows the operator to activate and/or deactivate system 10 or any component thereof separately (dispenser system 18, controller 28), to enter selection data indicating which of the capsules will be active, and/or to enter the mixing ratio. User interface 40 can be mounted on an encapsulation 42 of system 10.

In some embodiments, system 10 is remotely activated. In these embodiments, system 10 comprises a communication system 44 configured for communicating with a remote user interface 46. For example, user interface 46 can be a smart home control system, and controller 28 can transmit to the smart home control system, via communication system 44, signals pertaining to the state of system 10 and to receive from the smart home control system control signals than can include activation and/or deactivation signals, signals carrying selection data, signals carrying mixing ratio, and the like. The communication between interface 46 and communication system 44 can be via near field wireless communication technology. Correspondingly, interface 46 can be selected from a group consisting of a mobile phone, a tablet computer, and a notebook computer, which is provided with BLUETOOTH, Z-wave, ZigBee, or WIFI communication functions. The communication can also be via Internet, GPRS, GSM, CDMA, 3G, or 4 G communication technologies. Correspondingly, interface 46 can be a computer, which can be connected to Internet, or may be a mobile phone, which is provided with GPRS, GSM, CDMA, 3G, or 4 G communication functions. Other such ambiance effectors may be systems which modify the temperature, music or noise, alarm system, humidity, lighting and so on.

Figure 2:
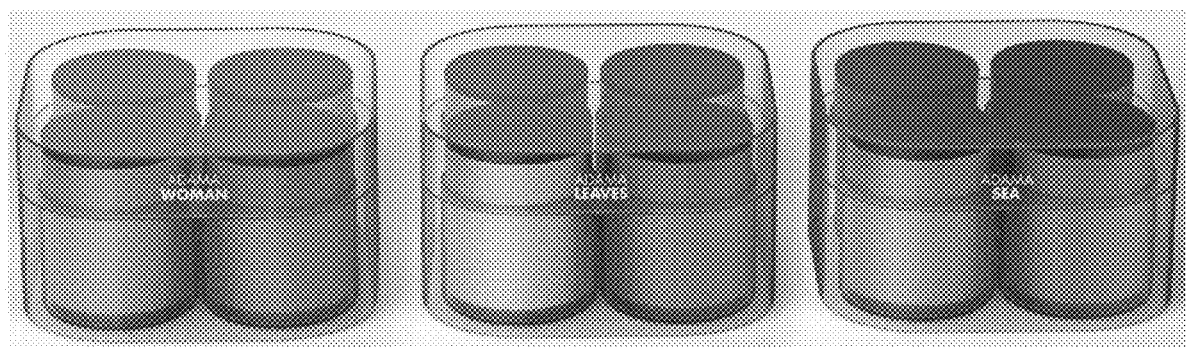
FIG. 2 is an image showing representative example of packages of edible material capsules, according to some embodiments of the present invention.

The duration of operation of each capsule is optionally and preferably from about 2 hours to about 24 hours. The capsules are preferably for a single use. The volume of edible material in each capsule can be from about 2 ml to about 10 ml. Other sizes and durations are not excluded from the scope of the present invention. The capsules can be provided to the consumer separately from system 10. For example, packages of several capsules can be marketed, wherein each package can include capsules containing the same or different edible materials. FIG. 2 is an image showing representative example of such packaging, wherein each package includes four capsules of the same edible material. Other packaging forms are also contemplated.

APPENDIX A

The edible material can, in some embodiments, comprise one or more substances having a CAS No. selected from the group consisting of: 50-21-5, 50-69-1, 50-81-7, 51-67-2, 51-79-6, 55-10-7, 56-12-2, 56-47-3, 56-81-5, 56-86-0, 56-93-9, 57-06-7, 57-11-4, 57-48-7, 57-50-1, 57-50-1, 58-08-2, 58-86-6, 59-02-9, 59-49-4, 59-92-7, 60-01-5, 60-12-8, 60-33-3, 60-33-3, 60-82-2, 62-49-7, 62-56-6, 64-04-0, 64-17-5, 64-18-6, 64-19-7, 65-85-0, 66-25-1, 67-03-8, 67-47-0, 67-63-0, 67-64-1, 68-39-3, 69-79-4, 70-53-1, 70-70-2, 71-23-8, 71-36-3, 71-41-0, 71-43-2, 72-17-3, 74-89-5, 74-93-1, 75-04-7, 75-07-0, 75-08-1, 75-18-3, 75-25-2, 75-31-0, 75-33-2, 75-50-3, 75-65-0, 75-66-1, 75-84-3, 75-85-4, 75-98-9, 76-22-2, 76-49-3, 76-50-6, 77-42-9, 77-53-2, 77-54-7, 77-70-3, 77-74-7, 77-83-8, 77-90-7, 77-92-9, 77-93-0, 78-35-3, 78-36-4, 78-37-5, 78-69-3, 78-70-6, 78-81-9, 78-83-1, 78-84-2, 78-92-2, 78-93-3, 78-94-4, 78-98-8, 79-06-1, 79-09-4, 79-11-8, 79-20-9, 79-31-2, 79-33-4, 79-42-5, 79-68-5, 79-69-6, 79-70-9, 79-76-5, 79-77-6, 79-78-7, 79-89-0, 79-92-5, 80-05-7, 80-26-2, 80-27-3, 80-46-6, 80-53-5, 80-56-8, 80-57-9, 80-59-1, 80-68-2, 80-71-7, 81-15-2, 83-34-1, 83-66-9, 83-67-0, 84-60-6, 85-32-5, 85-42-7, 85-44-9, 85-91-6, 87-05-8, 87-16-1, 87-19-4, 87-20-7, 87-22-9, 87-25-2, 87-29-6, 87-41-2, 87-44-5, 87-51-4, 87-55-8, 87-69-4, 87-91-2, 88-09-5, 88-14-2, 88-15-3, 88-18-6, 88-29-9, 88-60-8, 88-69-7, 88-84-6, 89-01-0, 89-43-0, 89-47-4, 89-48-5, 89-65-6, 89-72-5, 89-74-7, 89-78-1, 89-79-2, 89-80-5, 89-81-6, 89-82-7, 89-83-8, 89-86-1, 89-88-3, 89-95-2, 90-00-6, 90-02-8, 90-05-1, 90-12-0, 90-43-7, 90-80-2, 90-87-9, 91-02-1, 91-10-1, 91-16-7, 91-19-0, 91-22-5, 91-57-6, 91-60-1, 91-61-2, 91-62-3, 91-63-4, 91-87-2, 92-48-8, 92-53-5, 92-83-1, 93-02-7, 93-04-9, 93-08-3, 93-15-2, 93-16-3, 93-18-5, 93-28-7, 93-29-8, 93-44-7, 93-51-6, 93-53-8, 93-54-9, 93-55-0, 93-58-3, 93-60-7, 93-89-0, 93-91-4, 93-92-5, 94-02-0, 94-26-8, 94-30-4, 94-41-7, 94-46-2, 94-47-3, 94-48-4, 94-58-6, 94-62-2, 94-71-3, 94-86-0, 95-16-9, 95-20-5, 95-21-6, 95-41-0, 95-63-6, 95-65-8, 95-87-4, 95-92-1, 96-04-8, 96-09-3, 96-15-1, 96-17-3, 96-22-0, 96-26-4, 96-41-3, 96-47-9, 96-48-0, 96-54-8, 97-42-7, 97-45-0, 97-53-0, 97-54-1, 97-61-0, 97-62-1, 97-63-2, 97-64-3, 97-67-6, 97-85-8, 97-87-0, 97-89-2, 97-95-0, 97-96-1, 97-99-4, 98-00-0, 98-01-1, 98-02-2, 98-03-3, 98-11-3, 98-55-5, 98-83-9, 98-85-1, 98-86-2, 98-89-5, 98-97-5, 99-10-5, 99-48-9, 99-49-0, 99-50-3, 99-72-9, 99-75-2, 99-83-2, 99-85-4, 99-86-5, 99-87-6, 99-89-8, 99-93-4, 99-96-7, 100-06-1, 100-09-4, 100-51-6, 100-52-7, 100-53-8, 100-66-3, 100-68-5, 100-69-6, 100-71-0, 100-73-2, 100-83-4, 100-84-5, 100-86-7, 100-88-9, 101-39-3, 101-41-7, 101-48-4, 101-81-5, 101-84-8, 101-85-9, 101-86-0, 101-86-0, 101-94-0, 101-97-3, 102-04-5, 102-13-6, 102-16-9, 102-17-0, 102-19-2, 102-20-5, 102-22-7, 102-69-2, 102-76-1, 102-82-9, 102-94-3, 103-05-9, 103-07-1, 103-09-3, 103-13-9, 103-19-5, 103-23-1, 103-25-3, 103-26-4, 103-28-6, 103-36-6, 103-37-7, 103-38-8, 103-41-3, 103-43-5, 103-45-7, 103-48-0, 103-50-4, 103-52-6, 103-53-7, 103-54-8, 103-56-0, 103-58-2, 103-59-3, 103-60-6, 103-61-7, 103-64-0, 103-79-7, 103-82-2, 103-93-5, 104-09-6, 104-20-1, 104-21-2, 104-27-8, 104-45-0, 104-46-1, 104-50-7, 104-53-0, 104-54-1, 104-55-2, 104-57-4, 104-61-0, 104-62-1, 104-64-3, 104-65-4, 104-67-6, 104-76-7, 104-87-0, 104-90-5, 104-93-8, 105-01-1, 105-02-2, 105-13-5, 105-21-5, 105-26-0, 105-37-3, 105-43-1, 105-45-3, 105-46-4, 105-53-3, 105-54-4, 105-57-7, 105-66-8, 105-67-9, 105-68-0, 105-70-4, 105-75-9, 105-79-3, 105-82-8, 105-85-1, 105-86-2, 105-87-3, 105-89-5, 105-90-8, 105-91-9, 105-95-3, 106-02-5, 106-13-8, 106-18-3, 106-21-8, 106-22-9, 106-23-0, 106-24-1, 106-25-2, 106-26-3, 106-27-4, 106-28-5, 106-29-6, 106-30-9, 106-31-0, 106-32-1, 106-33-2, 106-34-3, 106-35-4, 106-36-5, 106-44-5, 106-45-6, 106-65-0, 106-67-2, 106-68-3, 106-70-7, 106-72-9, 106-73-0, 107-03-9, 107-10-8, 107-11-9, 107-18-6, 107-22-2, 107-31-3, 107-74-4, 107-75-5, 107-85-7, 107-86-8, 107-87-9, 107-92-6, 107-93-7, 107-95-9, 107-96-0, 108-10-1, 108-11-2, 108-21-4, 108-22-5, 108-29-2, 108-40-7, 108-47-4, 108-48-5, 108-50-9, 108-59-8, 108-64-5, 108-68-9, 108-73-6, 108-75-8, 108-82-7, 108-83-8, 108-89-4, 108-93-0, 108-98-5, 108-99-6, 109-00-2, 109-02-4, 109-05-7, 109-06-8, 109-08-0, 109-15-9, 109-19-3, 109-20-6, 109-21-7, 109-25-1, 109-29-5, 109-36-4, 109-42-2, 109-43-3, 109-49-9, 109-52-4, 109-60-4, 109-73-9, 109-79-5, 109-80-8, 109-92-2, 109-94-4, 109-95-7, 109-97-7, 109-99-9, 110-01-0, 110-02-1, 110-15-6, 110-19-0, 110-27-0, 110-29-2, 110-34-9, 110-38-3, 110-39-4, 110-40-7, 110-41-8, 110-42-9, 110-43-0, 110-45-2, 110-58-7, 110-62-3, 110-66-7, 110-71-4, 110-74-7, 110-77-0, 110-81-6, 110-85-0, 110-86-1, 110-89-4, 110-93-0, 110-94-1, 110-98-5, 111-06-8, 111-11-5, 111-12-6, 111-13-7, 111-14-8, 111-15-9, 111-26-2, 111-27-3, 111-28-4, 111-30-8, 111-31-9, 111-45-5, 111-47-7, 111-61-5, 111-62-6, 111-63-7, 111-68-2, 111-70-6, 111-71-7, 111-79-5, 111-80-8, 111-81-9, 111-82-0, 111-86-4, 111-87-5, 111-90-0, 112-05-0, 112-06-1, 112-12-9, 112-14-1, 112-17-4, 112-19-6, 112-23-2, 112-30-1, 112-31-2, 112-32-3, 112-37-8, 112-38-9, 112-39-0, 112-41-4, 112-42-5, 112-43-6, 112-44-7, 112-45-8, 112-46-9, 112-53-8, 112-54-9, 112-58-3, 112-59-4, 112-62-9, 112-63-0, 112-66-3, 112-70-9, 112-72-1, 112-73-2, 112-91-4, 114-76-1, 115-18-4, 115-19-5, 115-71-9, 115-95-7, 115-99-1, 116-02-9, 116-09-6, 116-26-7, 116-53-0, 116-66-5, 117-98-6, 118-58-1, 118-61-6, 118-71-8, 118-72-9, 118-93-4, 119-36-8, 119-53-9, 119-61-9, 119-65-3, 119-84-6, 120-11-6, 120-14-9, 120-24-1, 120-25-2, 120-29-6, 120-33-2, 120-45-6, 120-50-3, 120-51-4, 120-57-0, 120-72-9, 120-75-2, 120-92-3, 120-94-5, 121-32-4, 121-33-5, 121-34-6, 121-39-1, 121-98-2, 122-00-9, 122-03-2, 122-40-7, 122-43-0, 122-44-1, 122-45-2, 122-46-3, 122-48-5, 122-51-0, 122-57-6, 122-59-8, 122-62-3, 122-63-4, 122-67-8, 122-68-9, 122-69-0, 122-70-3, 122-71-4, 122-72-5, 122-74-7, 122-78-1, 122-78-1, 122-79-2, 122-84-9, 122-91-8, 122-95-2, 122-97-4, 122-99-6, 123-05-7, 123-07-9, 123-08-0, 123-11-5, 123-15-9, 123-19-3, 123-25-1, 123-29-5, 123-32-0, 123-32-0, 123-35-3, 123-38-6, 123-51-3, 123-66-0, 123-68-2, 123-69-3, 123-72-8, 123-73-9, 123-75-1, 123-76-2, 123-86-4, 123-92-2, 123-94-4, 123-95-5, 123-96-6, 124-04-9, 124-06-1, 124-07-2, 124-09-4, 124-10-7, 124-11-8, 124-13-0, 124-19-6, 124-25-4, 124-76-5, 125-12-2, 126-13-6, 126-14-7, 126-39-6, 126-64-7, 126-90-9, 126-91-0, 126-96-5, 127-06-0, 127-09-3, 127-17-3, 127-41-3, 127-42-4, 127-42-4, 127-42-4, 127-43-5, 127-51-5, 127-51-5, 127-51-5, 127-51-5, 127-51-5, 127-51-5, 127-91-3, 128-37-0, 128-50-7, 130-89-2, 131-17-9, 133-18-6, 133-21-1, 133-37-9, 134-01-0, 134-20-3, 134-28-1, 134-63-4, 134-64-5, 134-96-3, 135-02-4, 136-60-7, 137-00-8, 137-06-4, 137-32-6, 138-22-7, 138-23-8, 138-86-3, 138-87-4, 139-05-9, 139-45-7, 139-70-8, 139-85-5, 140-10-3, 140-11-4, 140-25-0, 140-26-1, 140-27-2, 140-39-6, 140-67-0, 141-03-7, 141-05-9, 141-06-0, 141-09-3, 141-10-6, 141-11-7, 141-12-8, 141-13-9, 141-14-0, 141-15-1, 141-16-2, 141-18-4, 141-25-3, 141-27-5, 141-28-6, 141-78-6, 141-79-7, 141-92-4, 141-97-9, 142-08-5, 142-19-8, 142-29-0, 142-47-2, 142-50-7, 142-60-9, 142-62-1, 142-68-7, 142-77-8, 142-83-6, 142-91-6, 142-92-7, 143-07-7, 143-08-8, 143-10-2, 143-13-5, 143-14-6, 144-39-8, 145-39-1, 149-32-6, 149-57-5, 150-19-6, 150-60-7, 150-69-6, 150-76-5, 150-78-7, 150-84-5, 150-86-7, 151-05-3, 151-10-0, 151-19-9, 154-17-6, 156-06-9, 157-06-2, 244-63-3, 287-27-4, 288-47-1, 289-16-7, 290-37-9, 291-22-5, 292-46-6, 294-62-2, 299-28-5, 301-00-8, 302-72-7, 312-84-5, 326-56-7, 326-61-4, 328-38-1, 328-39-2, 328-50-7, 334-48-5, 334-49-6, 348-67-4, 350-03-8, 352-93-2, 379-68-0, 404-86-4, 409-02-9, 420-12-2, 431-03-8, 432-24-6, 432-25-7, 434-13-9, 453-20-3, 454-29-5, 458-36-6, 459-80-3, 462-18-0, 462-95-3, 463-40-1, 464-07-3, 464-43-7, 464-45-9, 464-48-2, 464-49-3, 469-61-4, 470-67-7, 470-82-6, 472-66-2, 472-78-6, 472-97-9, 473-67-6, 475-03-6, 475-20-7, 488-10-8, 488-93-7, 488-97-1, 489-84-9, 490-03-9, 490-99-3, 491-01-0, 491-02-1, 491-04-3, 491-07-6, 491-09-8, 491-35-0, 491-37-2, 492-37-5, 492-62-6, 494-90-6, 494-99-5, 495-40-9, 495-61-4, 495-62-5, 495-76-1, 496-41-3, 496-77-5, 497-03-0, 497-19-8, 497-23-4, 497-38-1, 498-00-0, 498-02-2, 498-16-8, 498-66-8, 498-81-7, 499-12-7, 499-40-1, 499-54-7, 499-69-4, 499-70-7, 499-75-2, 500-02-7, 501-52-0, 501-92-8, 501-94-0, 502-26-1, 502-47-6, 502-61-4, 502-69-2, 502-99-8, 503-64-0, 503-74-2, 504-78-9, 504-85-8, 505-10-2, 505-29-3, 505-32-8, 505-57-7, 505-79-3, 506-52-5, 507-09-5, 507-70-0, 508-32-7, 511-59-1, 512-13-0, 512-61-8, 513-44-0, 513-53-1, 513-77-9, 513-85-9, 513-86-0, 514-99-8, 515-00-4, 515-03-7, 515-69-5, 520-26-3, 520-33-2, 526-75-0, 526-94-3, 526-95-4, 527-60-6, 527-72-0, 527-84-4, 528-43-8, 528-79-0, 529-20-4, 529-69-1, 530-31-4, 530-56-3, 530-57-4, 530-59-6, 531-26-0, 531-59-9, 532-28-5, 533-18-6, 533-31-3, 533-60-8, 533-67-5, 533-87-9, 534-15-6, 534-22-5, 535-77-3, 536-08-3, 536-45-8, 536-50-5, 536-59-4, 536-60-7, 536-75-4, 536-78-7, 538-65-8, 538-74-9, 538-86-3, 539-12-8, 539-30-0, 539-32-2, 539-82-2, 539-88-8, 539-90-2, 540-07-8, 540-18-1, 540-42-1, 540-63-6, 541-31-1, 541-35-5, 541-47-9, 541-58-2, 541-85-5, 541-91-3, 542-08-5, 542-28-9, 542-44-9, 542-46-1, 542-55-2, 542-85-8, 542-90-5, 543-39-5, 543-49-7, 544-12-7, 544-35-4, 544-40-1, 544-63-8, 546-28-1, 546-49-6, 546-79-2, 547-60-4, 547-63-7, 549-56-4, 551-08-6, 551-68-8, 551-93-9, 552-02-3, 552-63-6, 553-60-6, 553-79-7, 554-12-1, 554-14-3, 555-10-2, 556-24-1, 556-38-7, 556-61-6, 556-82-1, 557-00-6, 557-48-2, 562-74-3, 563-80-4, 564-20-5, 564-94-3, 565-60-6, 565-61-7, 565-63-9, 569-64-2, 571-58-4, 571-61-9, 575-41-7, 576-15-8, 576-26-1, 577-16-2, 577-85-5, 578-58-5, 579-07-7, 579-60-2, 579-74-8, 579-75-9, 579-93-1, 579-94-2, 580-72-3, 581-42-0, 582-62-7, 583-33-5, 583-58-4, 583-59-5, 583-60-8, 583-61-9, 583-92-6, 584-02-1, 584-08-7, 585-24-0, 585-25-1, 585-84-2, 585-88-6, 586-37-8, 586-38-9, 586-62-9, 586-82-3, 586-98-1, 588-67-0, 589-18-4, 589-34-4, 589-35-5, 589-38-8, 589-40-2, 589-43-5, 589-55-9, 589-59-3, 589-66-2, 589-75-3, 589-82-2, 589-90-2, 589-92-4, 589-98-0, 590-01-2, 590-29-4, 590-36-3, 590-66-9, 590-67-0, 590-73-8, 590-86-3, 591-11-7, 591-12-8, 591-22-0, 591-23-1, 591-24-2, 591-31-1, 591-47-9, 591-60-6, 591-63-9, 591-64-0, 591-68-4, 591-78-6, 591-80-0, 591-82-2, 591-87-7, 592-20-1, 592-43-8, 592-47-2, 592-82-5, 592-84-7, 592-88-1, 593-08-8, 593-26-0, 593-81-7, 593-84-0, 595-48-2, 597-49-9, 598-32-3, 598-75-4, 599-67-7, 600-14-6, 600-18-0, 600-22-6, 600-36-2, 601-34-3, 604-32-0, 604-33-1, 604-59-1, 604-68-2, 604-69-3, 606-45-1, 607-97-6, 608-68-4, 609-14-3, 609-36-9, 610-99-1, 611-13-2, 611-36-9, 611-70-1, 612-15-7, 612-16-8, 613-70-7, 613-75-2, 614-18-6, 614-29-9, 614-32-4, 614-47-1, 614-99-3, 615-10-1, 616-02-4, 616-06-8, 616-09-1, 616-25-1, 616-31-9, 616-44-4, 617-01-6, 617-02-7, 617-05-0, 617-29-8, 617-35-6, 617-50-5, 617-51-6, 617-57-2, 617-65-2, 617-74-3, 617-89-0, 617-90-3, 617-94-7, 618-45-1, 619-01-2, 620-02-0, 620-17-7, 620-23-5, 620-79-1, 620-80-4, 621-34-1, 621-82-9, 622-39-9, 622-45-7, 622-60-6, 622-78-6, 623-05-2, 623-13-2, 623-15-4, 623-17-6, 623-19-8, 623-20-1, 623-21-2, 623-22-3, 623-30-3, 623-36-9, 623-37-0, 623-42-7, 623-43-8, 623-70-1, 623-84-7, 623-91-6, 624-01-1, 624-09-9, 624-13-5, 624-17-9, 624-24-8, 624-41-9, 624-42-0, 624-45-3, 624-51-1, 624-54-4, 624-89-5, 624-92-0, 625-30-9, 625-33-2, 625-55-8, 625-60-5, 625-69-4, 625-80-9, 625-84-3, 625-86-5, 626-11-9, 626-38-0, 626-64-2, 626-67-5, 626-77-7, 626-82-4, 626-86-8, 626-89-1, 626-93-7, 626-98-2, 627-04-3, 627-77-0, 627-83-8, 627-88-3, 627-90-7, 627-91-8, 628-00-2, 628-03-5, 628-29-5, 628-46-6, 628-63-7, 628-97-7, 628-99-9, 629-05-0, 629-12-9, 629-19-6, 629-33-4, 629-40-3, 629-45-8, 629-59-4, 629-96-9, 632-15-5, 632-16-6, 633-31-8, 634-36-6, 636-72-6, 637-55-8, 637-64-9, 637-65-0, 637-78-5, 637-89-8, 638-00-6, 638-02-8, 638-10-8, 638-11-9, 638-17-5, 638-25-5, 638-37-9, 638-46-0, 638-49-3, 638-53-9, 638-65-3, 639-99-6, 644-08-6, 644-13-3, 644-35-9, 644-49-5, 644-98-4, 645-13-6, 645-17-0, 645-56-7, 645-62-5, 645-67-0, 645-69-2, 645-72-7, 646-01-5, 646-07-1, 646-13-9, 656-53-1, 657-26-1, 659-70-1, 661-19-8, 672-15-1, 673-22-3, 673-84-7, 674-76-0, 676-47-1, 688-82-4, 689-67-8, 689-89-4, 691-38-3, 692-86-4, 693-38-9, 693-54-9, 693-95-8, 695-06-7, 696-30-0, 696-59-3, 696-63-9, 698-10-2, 698-27-1, 698-76-0, 698-87-3, 699-02-5, 699-10-5, 699-17-2, 700-82-3, 701-70-2, 701-97-3, 702-23-8, 705-73-7, 705-76-0, 705-86-2, 706-14-9, 710-04-3, 713-95-1, 730-46-1, 759-05-7, 762-29-8, 763-32-6, 763-69-9, 764-37-4, 764-38-5, 764-39-6, 764-40-9, 764-67-0, 765-70-8, 765-87-7, 766-92-7, 770-27-4, 774-48-1, 774-64-1, 804-63-7, 814-67-5, 816-11-5, 816-66-0, 816-79-5, 817-88-9, 818-04-2, 818-38-2, 818-57-5, 818-58-6, 818-81-5, 819-97-6, 820-00-8, 821-09-0, 821-41-0, 821-55-6, 823-22-3, 823-76-7, 828-26-2, 829-26-5, 866-82-0, 867-56-1, 868-57-5, 870-23-5, 871-22-7, 872-10-6, 872-55-9, 872-85-5, 873-64-3, 873-94-9, 874-66-8, 877-22-5, 877-60-1, 880-36-4, 881-68-5, 882-33-7, 909-84-2, 923-27-3, 923-69-3, 924-88-9, 925-15-5, 925-16-6, 925-47-3, 925-54-2, 925-78-0, 927-49-1, 928-68-7, 928-80-3, 928-91-6, 928-94-9, 928-95-0, 928-96-1, 928-97-2, 928-98-3, 930-68-7, 932-16-1, 933-67-5, 937-05-3, 937-30-4, 937-94-0, 939-21-9, 939-23-1, 939-27-5, 939-48-0, 941-43-5, 941-98-0, 942-92-7, 943-88-4, 949-67-7, 996-31-6, 999-40-6, 1002-84-2, 1003-03-8, 1003-04-9, 1003-10-7, 1003-14-1, 1003-29-8, 1003-31-2, 1003-38-9, 1004-29-1, 1009-62-7, 1071-73-4, 1072-72-6, 1072-83-9, 1073-11-6, 1073-26-3, 1073-29-6, 1076-56-8, 1078-95-1, 1079-01-2, 1080-12-2, 1083-41-6, 1113-13-9, 1113-21-9, 1113-60-6, 1114-92-7, 1115-11-3, 1115-30-6, 1115-84-0, 1117-31-3, 1117-41-5, 1117-52-8, 1117-55-1, 1117-59-5, 1117-61-9, 1117-65-3, 1118-27-0, 1118-39-4, 1118-71-4, 1118-84-9, 1119-06-8, 1119-16-0, 1119-34-2, 1119-44-4, 1119-60-4, 1121-24-0, 1121-60-4, 1122-54-9, 1122-62-9, 1122-70-9, 1123-85-9, 1123-96-2, 1124-11-4, 1124-20-5, 1125-21-9, 1125-88-8, 1126-79-0, 1128-08-1, 1129-30-2, 1129-67-5, 1129-69-7, 1135-23-5, 1139-30-6, 1142-85-4, 1154-92-3, 1162-65-8, 1165-39-5, 1166-52-5, 1182-07-6, 1182-42-9, 1183-04-6, 1184-64-1, 1184-78-7, 1188-02-9, 1188-37-0, 1189-09-9, 1191-03-3, 1191-04-4, 1191-08-8, 1191-16-8, 1191-41-9, 1191-43-1, 1191-62-4, 1192-58-1, 1192-62-7, 1193-11-9, 1193-18-6, 1193-79-9, 1195-09-1, 1195-14-8, 1195-32-0, 1195-79-5, 1195-92-2, 1196-01-6, 1196-22-1, 1196-31-2, 1197-01-9, 1197-15-5, 1197-20-2, 1197-40-6, 1200-67-5, 1205-17-0, 1205-42-1, 1205-91-0, 1209-61-6, 1211-29-6, 1227-51-6, 1245-15-4, 1249-81-6, 1313-60-6, 1319-88-6, 1321-30-8, 1321-89-7, 1322-17-4, 1323-00-8, 1323-75-7, 1329-99-3, 1331-92-6, 1333-09-1, 1334-78-7, 1334-82-3, 1335-08-6, 1335-48-4, 1335-66-6, 1335-86-0, 1337-83-3, 1338-41-6, 1338-80-3, 1365-19-1, 1401-55-4, 1405-86-3, 1424-83-5, 1436-34-6, 1438-91-1, 1438-94-4, 1450-72-2, 1450-85-7, 1454-84-8, 1455-20-5, 1455-21-6, 1460-34-0, 1463-01-0, 1487-49-6, 1489-56-1, 1489-57-2, 1490-04-6, 1501-82-2, 1504-74-1, 1504-75-2, 1515-80-6, 1515-81-7, 1515-95-3, 1516-17-2, 1534-08-3, 1540-28-9, 1540-29-0, 1551-27-5, 1551-43-5, 1551-44-6, 1552-67-6, 1561-11-1, 1565-76-0, 1565-80-6, 1565-81-7, 1569-02-4, 1569-50-2, 1569-60-4, 1569-69-3, 1575-74-2, 1576-77-8, 1576-78-9, 1576-85-8, 1576-87-0, 1576-95-0, 1576-96-1, 1577-18-0, 1577-19-1, 1587-20-8, 1599-47-9, 1599-49-1, 1604-28-0, 1604-34-8, 1608-72-6, 1609-47-8, 1617-23-8, 1617-25-0, 1617-32-9, 1617-37-4, 1617-40-9, 1618-26-4, 1628-89-3, 1629-58-9, 1629-60-3, 1632-73-1, 1634-04-4, 1635-02-5, 1635-31-0, 1637-24-7, 1639-09-4, 1653-30-1, 1669-44-9, 1670-46-8, 1670-47-9, 1673-08-1, 1674-08-4, 1679-07-8, 1679-09-0, 1694-09-3, 1700-37-4, 1703-52-2, 1706-12-3, 1708-29-8, 1708-35-6, 1708-36-7, 1708-39-0, 1708-81-2, 1708-82-3, 1721-89-7, 1724-02-3, 1725-03-7, 1727-68-0, 1731-81-3, 1731-84-6, 1732-09-8, 1732-10-1, 1733-25-1, 1741-41-9, 1746-13-0, 1754-62-7, 1759-28-0, 1775-43-5, 1779-60-8, 1786-08-9, 1795-01-3, 1797-74-6, 1802-20-6, 1820-09-3, 1838-59-1, 1864-97-7, 1866-31-5, 1871-67-6, 1878-18-8, 1883-75-6, 1883-78-9, 1888-90-0, 1901-26-4, 1901-38-8, 1908-11-8, 1946-00-5, 1949-89-9, 1963-36-6, 1968-40-7, 1987-50-4, 1989-52-2, 2009-74-7, 2021-28-5, 2024-70-6, 2035-99-6, 2044-73-7, 2046-17-5, 2049-80-1, 2049-96-9, 2050-01-3, 2050-08-0, 2050-09-1, 2050-23-9, 2050-87-5, 2051-04-9, 2051-50-5, 2051-78-7, 2051-96-9, 2052-14-4, 2052-15-5, 2065-23-8, 2078-54-8, 2079-95-0, 2084-18-6, 2084-19-7, 2092-49-1, 2094-69-1, 2100-17-6, 2102-59-2, 2108-05-6, 2110-18-1, 2110-78-3, 2111-75-3, 2116-65-6, 2127-03-9, 2142-94-1, 2153-26-6, 2153-28-8, 2167-14-8, 2173-56-0, 2173-57-1, 2177-77-7, 2179-57-9, 2179-58-0, 2179-59-1, 2179-60-4, 2186-92-7, 2198-61-0, 2216-45-7, 2216-51-5, 2216-52-6, 2216-69-5, 2216-81-1, 2217-33-6, 2217-35-8, 2230-90-2, 2234-20-0, 2235-83-8, 2239-78-3, 2244-16-8, 2244-16-8, 2245-85-1, 2245-38-7, 2253-73-8, 2257-09-2, 2270-60-2, 2277-16-9, 2277-19-2, 2278-53-7, 2294-76-0, 2305-05-7, 2305-21-7, 2305-25-1, 2306-78-7, 2306-88-9, 2306-91-4, 2307-10-0, 2308-

18-1, 2311-46-8, 2311-59-3, 2315-09-5, 2315-68-6, 2315-97-1, 2316-26-9, 2344-70-9, 2345-24-6, 2345-26-8, 2345-27-9, 2345-28-0, 2346-00-1, 2349-07-7, 2349-13-5, 2351-90-8, 2363-88-4, 2363-89-5, 2371-13-3, 2379-55-7, 2380-78-1, 2385-77-5, 2396-77-2, 2396-78-3, 2396-83-0, 2396-84-1, 2396-85-2, 2403-58-9, 2407-43-4, 2408-20-0, 2408-37-9, 2412-73-9, 2412-80-8, 2416-94-6, 2432-42-0, 2432-51-1, 2432-77-1, 2432-83-9, 2432-91-9, 2437-23-2, 2438-20-2, 2439-44-3, 2442-10-6, 2444-46-4, 2444-49-7, 2445-67-2, 2445-69-4, 2445-72-9, 2445-76-3, 2445-77-4, 2445-78-5, 2445-83-2, 2445-93-4, 2449-49-2, 2463-53-8, 2463-63-0, 2463-77-6, 2464-23-5, 2465-32-9, 2478-38-8, 2482-39-5, 2491-06-7, 2492-87-7, 2495-35-4, 2495-37-6, 2497-18-9, 2497-21-4, 2499-95-8, 2518-53-8, 2524-52-9, 2527-76-6, 2530-10-1, 2539-53-9, 2545-22-4, 2548-87-0, 2550-18-7, 2550-26-7, 2550-40-5, 2556-10-7, 2566-89-4, 2568-25-4, 2584-71-6, 2601-13-0, 2623-23-6, 2623-91-8, 2628-17-3, 2630-39-9, 2637-34-5, 2639-63-6, 2679-87-0, 2690-08-6, 2705-87-5, 2719-08-6, 2721-22-4, 2756-56-1, 2758-18-1, 2765-04-0, 2777-58-4, 2785-87-7, 2785-89-9, 2806-85-1, 2810-04-0, 2835-39-4, 2847-30-5, 2847-30-5, 2882-20-4, 2882-21-5, 2882-22-6, 2884-13-1, 2884-14-2, 2906-55-0, 27615-31-2, 2917-26-2, 2931-90-0, 2949-92-0, 2983-36-0, 2983-37-1, 2983-38-2, 2985-28-6, 2998-04-1, 3008-43-3, 3016-19-1, 3025-30-7, 3033-23-6, 3050-69-9, 3054-92-0, 3080-69-1, 3089-55-2, 3121-70-8, 3130-87-8, 3142-66-3, 3142-72-1, 3149-28-8, 3150-24-1, 3153-44-4, 3184-13-2, 3188-00-9, 3194-17-0, 3208-16-0, 3208-40-0, 3230-94-2, 3240-09-3, 3249-68-1, 3254-39-5, 3268-49-3, 3269-90-7, 3289-28-9, 3293-47-8, 3299-32-9, 3301-90-4, 3301-94-8, 3302-03-2, 3319-99-1, 3338-55-4, 3360-41-6, 3374-22-9, 3381-26-8, 3386-97-8, 3387-41-5, 3390-12-3, 3391-86-4, 3391-87-5, 3452-97-9, 3454-07-7, 3454-28-2, 3460-37-5, 3460-44-4, 3468-63-1, 3487-99-8, 3489-28-9, 3491-63-2, 3511-32-8, 3520-72-7, 3521-91-3, 3549-23-3, 3558-60-9, 3570-55-6, 3572-06-3, 3581-87-1, 3581-91-7, 3586-14-9, 3600-24-6, 3603-99-4, 3615-41-6, 3623-51-6, 3623-52-7, 3637-01-2, 3637-14-7, 3637-16-9, 3658-77-3, 3658-77-3, 3658-79-5, 3658-80-8, 3658-92-2, 3658-93-3, 3658-94-4, 3658-95-5, 3669-80-5, 3681-71-8, 3681-78-5, 3681-82-1, 3682-42-6, 3687-48-7, 3691-12-1, 3698-95-1, 3715-29-5, 3715-31-9, 3720-16-9, 3724-55-8, 3724-61-6, 3724-65-0, 3738-00-9, 3746-40-5, 3757-32-2, 3760-11-0, 3773-93-1, 3777-69-3, 3777-71-7, 3779-61-1, 3780-58-3, 3782-00-1, 3796-70-1, 3842-03-3, 3848-24-6, 3857-25-8, 3876-52-6, 3877-15-4, 3891-59-6, 3913-71-1, 3913-80-2, 3913-81-3, 3913-85-7, 3915-83-1, 3934-81-4, 3938-95-2, 3943-74-6, 4001-61-0, 4023-65-8, 4032-80-8, 4049-38-1, 4050-45-7, 4077-47-8, 4100-80-5, 4104-45-4, 4110-50-3, 4112-89-4, 4112-92-9, 4121-13-5, 4124-63-4, 4124-88-3, 4131-76-4, 4151-33-1, 4166-20-5, 4175-66-0, 4177-16-6, 4179-38-8, 4180-23-8, 4192-90-9, 4195-88-4, 4206-58-0, 4208-49-5, 4208-57-5, 4208-61-1, 4219-24-3, 4221-03-8, 4221-98-1, 4229-91-8, 4230-97-1, 4253-89-8, 4265-16-1, 4265-25-2, 4265-97-8, 4276-68-0, 4312-99-6, 4313-03-5, 4320-30-3, 4346-18-3, 4351-10-4, 4351-54-6, 4351-55-7, 4352-99-2, 4353-01-9, 4359-46-0, 4359-54-0, 4360-60-5, 4364-06-1, 4373-34-6, 4383-05-5, 4395-92-0, 4396-62-7, 4403-20-7, 4404-45-9, 4410-99-5, 4411-89-6, 4426-79-3, 4426-83-9, 4430-31-3, 4430-36-8, 4430-39-1, 4430-42-6, 4430-45-9, 4433-36-7, 4436-82-2, 4437-20-1, 4437-22-3, 4437-51-8, 4440-65-7, 4442-79-9, 4450-94-6, 4455-13-4, 4466-24-4, 4485-09-0, 4493-42-9, 4500-58-7, 4501-58-0, 4502-00-5, 4516-90-9, 4532-64-3, 4536-23-6, 4536-26-9, 4573-50-6, 4602-84-0, 4606-15-9, 4630-07-3, 4630-82-4, 4634-89-3, 4643-25-8, 4643-27-8, 4673-31-8, 4674-50-4, 4675-87-0, 4680-78-8, 4691-65-0, 4691-65-0, 4695-62-9, 4706-81-4, 4720-29-0, 4728-82-9, 4732-13-2, 4744-08-5, 4744-10-9, 4747-07-3, 4747-61-9, 4748-78-1, 4752-86-7, 4795-29-3, 4798-44-1, 4798-61-2, 4810-79-1, 4826-62-4, 4858-85-9, 4861-58-9, 4861-85-2, 4864-61-3, 4868-20-6, 4883-60-7, 4884-24-6, 4887-30-3, 4900-30-5, 4906-24-5, 4938-52-7, 4940-11-8, 4951-48-8, 4984-85-4, 5009-32-5, 5058-19-5, 5076-72-2, 5077-67-8, 5090-41-5, 5090-63-1, 5129-47-5, 5129-48-6, 5132-75-2, 5137-52-0, 5141-20-8, 5146-66-7, 5153-25-3, 5163-67-7, 5164-78-3, 5166-53-0, 5205-07-2, 5205-10-7, 5205-11-8, 5205-12-9, 5208-59-3, 5263-87-6, 5271-38-5, 5287-45-6, 5292-21-7, 5296-64-0, 5298-13-5, 5303-26-4, 5320-75-2, 5323-87-5, 5328-37-0, 5331-32-8, 5331-37-3, 5331-48-6, 5333-83-5, 5340-36-3, 5348-74-3, 5349-60-0, 5349-62-2, 5350-03-8, 5355-17-9, 5355-63-5, 5362-56-1, 5368-81-0, 5392-40-5, 5392-40-5, 5394-83-2, 5396-89-4, 5405-41-4, 5405-58-3, 5406-12-2, 5406-18-8, 5413-49-0, 5417-30-1, 5420-17-7, 5421-00-1, 5421-04-5, 5421-12-5, 5421-17-0, 5421-27-2, 5421-99-8, 5422-34-4, 5424-01-1, 5424-19-1, 5432-85-9, 5435-64-3, 5436-21-5, 5444-75-7, 5451-57-0, 5451-87-6, 5451-88-7, 5451-95-6, 5452-07-3, 5452-75-5, 5454-09-1, 5454-11-5, 5454-12-6, 5454-19-3, 5454-21-7, 5454-28-4, 5455-24-3, 5457-70-5, 5457-86-3, 5458-59-3, 5460-45-7, 5460-46-8, 5461-06-3, 5461-08-5, 5466-06-8, 5468-05-3, 5468-06-4, 5468-23-5, 5468-75-7, 5471-51-2, 5502-75-0, 5524-05-0, 5533-03-9, 5550-12-9, 5552-30-7, 5555-90-8, 5577-44-6, 5579-78-2, 5585-39-7, 5601-60-5, 5604-55-7, 5616-51-3, 5617-64-1, 5650-43-1, 5655-61-8, 5660-60-6, 5669-09-0, 5694-82-6, 5698-27-1, 5703-26-4, 5718-75-2, 5724-81-2, 5739-17-3, 5756-24-1, 5760-50-9, 5794-03-6, 5794-04-7, 5820-89-3, 5837-78-5, 5862-47-5, 5870-68-8, 5870-93-9, 5897-45-0, 5905-46-4, 5905-47-5, 5910-85-0, 5910-87-2, 5910-89-4, 5921-82-4, 5921-83-5, 5925-68-8, 5925-75-7, 5933-87-9, 5943-30-6, 5943-34-0, 5947-36-4, 5949-05-3, 5953-49-1, 5978-70-1, 5980-15-4, 5986-38-9, 5988-91-0, 5989-27-5, 5989-33-3, 5989-54-8, 5996-22-5, 6004-38-2, 6007-26-7, 6028-07-5, 6028-61-1, 6030-14-4, 6032-29-7, 6044-68-4, 6051-03-2, 6066-49-5, 6070-14-0, 6070-16-2, 6079-97-6, 6089-09-4, 6091-50-5, 6093-95-4, 6099-03-2, 6099-04-3, 6117-91-5, 6119-47-7, 6119-70-6, 6126-50-7, 6132-04-3, 6138-23-4, 6164-79-0, 6169-06-8, 6175-49-1, 6189-76-0, 6191-71-5, 6203-18-5, 6208-91-9, 6221-93-8, 6222-35-1, 6243-10-3, 6248-20-0, 6258-60-2, 6258-63-5, 6259-76-3, 6259-77-4, 6261-18-3, 6263-65-6, 6270-34-4, 6270-55-9, 6270-56-0, 6280-99-5, 6281-40-9, 6283-86-9, 6283-92-7, 6284-46-4, 6290-13-7, 6290-14-8, 6290-17-1, 6290-20-6, 6290-37-5, 6293-37-4, 6294-31-1, 6297-48-9, 6301-70-8, 6304-24-1, 6309-51-9, 6309-62-2, 6314-97-2, 6316-16-1, 6316-54-7, 6320-18-9, 6321-45-5, 6329-01-7, 6330-67-2, 6342-56-9, 6358-85-6, 6378-65-0, 6379-73-3, 6380-23-0, 6380-28-5, 6381-92-6, 6382-06-5, 6413-10-1, 6414-32-0, 6424-12-0, 6428-31-5, 6443-92-1, 6454-22-4, 6471-66-5, 6471-96-1, 6485-34-3, 6485-40-1, 6513-03-7, 6540-86-9, 6540-98-3, 6553-81-7, 6561-39-3, 6588-78-9, 6622-76-0, 6624-58-4, 6624-71-1, 6627-88-9, 6628-18-8, 6635-22-9, 6638-05-7, 6725-64-0, 6728-26-3, 6728-31-0, 6738-23-4, 6750-03-4, 6753-98-6, 6766-82-1, 6789-80-6, 6789-88-4, 6790-58-5, 6812-78-8, 6839-75-4, 6849-18-9, 6890-26-2, 6890-27-3, 6893-26-1, 6901-97-9, 6911-51-9, 6915-15-7, 6924-68-1, 6938-33-6, 6938-45-0, 6939-75-9, 6940-09-6, 6947-02-0, 6951-08-2, 6963-40-2, 6963-44-6, 6963-56-0, 6971-51-3, 6975-24-2, 6975-60-6, 6976-72-3, 6982-72-5, 6986-51-2, 7011-83-8, 7053-79-4, 7069-41-2, 7111-29-7, 7143-69-3, 7148-78-9, 7149-26-0, 7149-29-3, 7149-32-8, 7155-12-6, 7207-49-0, 7212-40-0, 7212-44-4, 7216-56-0, 7217-59-6, 7220-81-7, 7241-98-7, 7251-61-8, 7274-88-6, 7299-91-4, 7311-34-4, 7314-44-5, 7318-67-4, 7322-

63-6, 7328-34-9, 7335-26-4, 7341-17-5, 7361-80-0, 7367-78-4, 7367-81-9, 7367-82-0, 7367-83-1, 7367-84-2, 7367-85-3, 7367-88-6, 7367-90-0, 7370-44-7, 7370-92-5, 7384-98-7, 7386-24-5, 7392-19-0, 7399-49-7, 7402-29-1, 7416-35-5, 7417-18-7, 7425-15-2, 7434-89-1, 7447-40-7, 7452-79-1, 7460-74-4, 7462-24-0, 7492-37-7, 7492-39-9, 7492-41-3, 7492-44-6, 7492-45-7, 7492-65-1, 7492-66-2, 7492-67-3, 7492-69-5, 7492-70-8, 7493-57-4, 7493-58-5, 7493-59-6, 7493-63-2, 7493-65-4, 7493-66-5, 7493-68-7, 7493-69-8, 7493-71-2, 7493-72-3, 7493-74-5, 7493-75-6, 7493-76-7, 7493-78-9, 7493-79-0, 7493-80-3, 7493-82-5, 7493-95-0, 7500-42-7, 7504-66-7, 7533-07-5, 7540-51-4, 7540-53-6, 7541-49-3, 7549-33-9, 7549-37-3, 7549-41-9, 7553-56-2, 7554-12-3, 7558-63-6, 7563-33-9, 7585-39-9, 7598-60-9, 7631-94-9, 7646-78-8, 7646-79-9, 7647-14-5, 7681-88-1, 7688-21-3, 7699-45-8, 7704-73-6, 7726-03-6, 7732-18-5, 7756-96-9, 7764-50-3, 7774-44-9, 7774-47-2, 7774-60-9, 7774-65-4, 7774-73-4, 7774-74-5, 7774-79-0, 7774-82-5, 7774-96-1, 7775-00-0, 7775-38-4, 7775-39-5, 7776-28-5, 7778-80-5, 7778-83-8, 7778-87-2, 7778-96-3, 7779-07-9, 7779-16-0, 7779-17-1, 7779-23-9, 7779-30-8, 7779-41-1, 7779-50-2, 7779-54-6, 7779-65-9, 7779-66-0, 7779-67-1, 7779-70-6, 7779-72-8, 7779-73-9, 7779-75-1, 7779-77-3, 7779-78-4, 7779-80-5, 7779-81-9, 7779-94-4, 7780-06-5, 7781-98-8, 7782-49-2, 7784-67-0, 7784-98-7, 7785-26-4, 7785-33-3, 7785-53-7, 7785-54-8, 7785-63-9, 7785-64-0, 7785-65-1, 7785-70-8, 7786-29-0, 7786-30-3, 7786-44-9, 7786-47-2, 7786-48-3, 7786-58-5, 7786-61-0, 7786-67-6, 7787-20-4, 7789-92-6, 7790-28-5, 7803-63-6, 7803-65-8, 8000-25-7, 8000-25-7, 8000-25-7, 8000-25-7, 8000-25-7, 8000-25-7, 8000-25-7, 8000-25-7, 8000-25-7, 8000-26-8, 8000-28-0, 8000-28-0, 8000-28-0, 8000-28-0, 8000-28-0, 8000-28-0, 8000-28-0, 8000-28-0, 8000-29-1, 8000-34-8, 8000-34-8, 8000-34-8, 8000-34-8, 8000-34-8, 8000-41-7, 8000-42-8, 8000-42-8, 8000-44-0, 8000-44-0, 8000-46-2, 8000-46-2, 8000-46-2, 8000-46-2, 8000-46-2, 8000-48-4, 8000-48-4, 8000-48-4, 8000-48-4, 8000-48-4, 8000-48-4, 8000-66-6, 8000-66-6, 8000-68-8, 8000-68-8, 8000-68-8, 8000-68-8, 8000-68-8, 8000-78-0, 8000-78-0, 8000-78-0, 8000-78-0, 8001-04-5, 8001-25-0, 8001-25-0, 8001-25-0, 8001-31-8, 8001-31-8, 8001-31-8, 8001-48-7, 8001-58-9, 8001-76-1, 8001-76-1, 8002-03-7, 8002-03-7, 8002-09-3, 8002-13-9, 8002-48-0, 8002-56-0, 8002-60-6, 8002-60-6, 8002-66-2, 8002-66-2, 8002-72-0, 8002-72-0, 8002-72-0, 8002-72-0, 8002-72-0, 8002-72-0, 8002-73-1, 8002-73-1, 8002-73-1, 8002-73-1, 8002-73-1, 8005-33-2, 8006-64-2, 8006-75-5, 8006-75-5, 8006-75-5, 8006-75-5, 8006-75-5, 8006-75-5, 8006-75-5, 8006-77-7, 8006-77-7, 8006-77-7, 8006-77-7, 8006-77-7, 8006-77-7, 8006-78-8, 8006-81-3, 8006-81-3, 8006-81-3, 8006-81-3, 8006-82-4, 8006-82-4, 8006-82-4, 8006-83-5, 8006-84-6, 8006-86-8, 8006-87-9, 8006-87-9, 8006-90-4, 8006-90-4, 8006-90-4, 8006-90-4, 8006-90-4, 8006-90-4, 8006-90-4, 8006-90-4, 8006-90-4, 8006-90-4, 8006-90-4, 8007-00-9, 8007-00-9, 8007-00-9, 8007-01-0, 8007-01-0, 8007-01-0, 8007-01-0, 8007-01-0, 8007-01-0, 8007-01-0, 8007-02-1, 8007-02-1, 8007-04-3, 8007-04-3, 8007-06-5, 8007-08-7, 8007-08-7, 8007-08-7, 8007-08-7, 8007-08-7, 8007-11-2, 8007-11-2, 8007-11-2, 8007-12-3, 8007-12-3, 8007-20-3, 8007-27-0, 8007-35-0, 8007-40-7, 8007-40-7, 8007-46-3, 8007-46-3, 8007-46-3, 8007-46-3, 8007-48-5, 8007-48-5, 8007-48-5, 8007-70-3, 8007-70-3, 8007-70-3, 8007-70-3, 8007-70-3, 8007-75-8, 8007-75-8, 8007-75-8, 8007-75-8, 8007-75-8, 8007-75-8, 8007-78-1, 8007-78-1, 8007-80-5, 8007-80-5, 8007-80-5, 8007-87-2, 8007-87-2, 8007-93-0, 8007-93-0, 8008-26-2, 8008-26-2, 8008-26-2, 8008-26-2, 8008-26-2, 8008-26-2, 8008-26-2, 8008-26-2, 8008-26-2, 8008-26-2, 8008-26-2, 8008-26-2, 8008-26-2, 8008-26-2, 8008-31-9, 8008-31-9, 8008-31-9, 8008-31-9, 8008-31-9, 8008-31-9, 8008-31-9, 8008-31-9, 8008-31-9, 8008-31-9, 8008-31-9, 8008-45-5, 8008-45-5, 8008-45-5, 8008-45-5, 8008-45-5, 8008-51-3, 8008-52-4, 8008-52-4, 8008-52-4, 8008-52-4, 8008-56-8, 8008-56-8, 8008-56-8, 8008-56-8, 8008-56-8, 8008-56-8, 8008-56-8, 8008-56-8, 8008-56-8, 8008-56-8, 8008-56-8, 8008-56-8, 8008-56-8, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-74-0, 8008-74-0, 8008-74-0, 8008-74-0, 8008-79-5, 8008-79-5, 8008-79-5, 8008-79-5, 8008-80-8, 8008-88-6, 8008-88-6, 8008-93-3, 8008-93-3, 8008-93-3, 8008-93-3, 8008-98-8, 8008-98-8, 8008-99-9, 8008-99-9, 8012-89-3, 8012-89-3, 8012-91-7, 8013-01-2, 8013-12-5, 8013-75-0, 8013-76-1, 8013-90-9, 8013-97-6, 8013-99-8, 8013-99-8, 8014-09-3, 8014-09-3, 8014-09-3, 8014-09-3, 8014-09-3, 8014-09-3, 8014-13-9, 8014-13-9, 8014-17-3, 8014-17-3, 8014-17-3, 8014-17-3, 8014-17-3, 8014-17-3, 8014-17-3, 8014-19-5, 8014-29-7, 8014-71-9, 8015-01-8, 8015-01-8, 8015-01-8, 8015-01-8, 8015-62-1, 8015-62-1, 8015-64-3, 8015-64-3, 8015-64-3, 8015-64-3, 8015-64-3, 8015-64-3, 8015-73-4, 8015-73-4, 8015-73-4, 8015-73-4, 8015-73-4, 8015-73-4, 8015-73-4, 8015-73-4, 8015-77-8, 8015-77-8, 8015-77-8, 8015-88-1, 8015-88-1, 8015-88-1, 8015-88-1, 8015-89-2, 8015-89-2, 8015-90-5, 8015-90-5, 8015-90-5, 8015-91-6, 8015-91-6, 8015-91-6, 8015-91-6, 8015-91-6, 8015-91-6, 8015-92-7, 8015-92-7, 8015-92-7, 8016-03-3, 8016-03-3, 8016-20-4, 8016-20-4, 8016-20-4, 8016-20-4, 8016-20-4, 8016-20-4, 8016-20-4, 8016-20-4, 8016-20-4, 8016-20-4, 8016-21-5, 8016-21-5, 8016-23-7, 8016-25-9, 8016-26-0, 8016-26-0, 8016-26-0, 8016-31-7, 8016-31-7, 8016-31-7, 8016-36-2, 8016-36-2, 8016-37-3, 8016-37-3, 8016-37-3, 8016-37-3, 8016-38-4, 8016-38-4, 8016-38-4, 8016-38-4, 8016-42-0, 8016-63-5, 8016-63-5, 8016-63-5, 8016-63-5, 8016-63-5, 8016-63-5, 8016-63-5, 8016-63-5, 8016-63-5, 8016-68-0, 8016-69-1, 8016-78-2, 8016-78-2, 8016-79-3, 8016-84-0, 8016-84-0, 8016-84-0, 8016-84-0, 8016-84-0, 8016-84-0, 8016-84-0, 8016-84-0, 8016-84-0, 8016-84-0, 8016-85-1, 8016-85-1, 8016-85-1, 8016-85-1, 8016-85-1, 8016-88-4, 8016-94-2, 8021-29-2, 8021-39-4, 8022-07-9, 8022-07-9, 8022-07-9, 8022-07-9, 8022-15-9, 8022-15-9, 8022-15-9, 8022-18-2, 8022-56-8, 8022-56-8, 8022-56-8, 8022-56-8, 8022-56-8, 8022-56-8, 8022-56-8, 8022-56-8, 8022-56-8, 8022-56-8, 8022-96-6, 8022-96-6, 8022-96-6, 8022-96-6, 8022-96-6, 8022-96-6, 8022-96-6, 8022-96-6, 8022-96-6, 8023-76-5, 8023-77-6, 8023-77-6, 8023-78-7, 8023-78-7, 8023-83-4, 8023-83-4, 8023-83-4, 8023-83-4, 8023-88-9, 8023-88-9, 8023-89-0, 8023-89-0, 8023-89-0, 8023-91-4, 8023-91-4, 8023-99-2, 8023-99-2, 8023-99-2, 8023-99-2, 8024-00-8, 8024-03-1, 8024-05-3, 8024-05-3, 8024-06-4, 8024-06-4, 8024-06-4, 8024-08-6, 8024-08-6, 8024-15-5, 8024-40-6, 8025-95-4, 8025-95-4, 8028-47-5, 8028-48-6, 8028-48-6, 8028-48-6, 8028-48-6, 8028-48-6, 8028-48-6, 8028-66-8, 8028-66-8, 8029-31-0, 8029-81-0, 8030-28-2, 8030-28-2, 8030-28-2, 8030-28-2, 8030-89-5, 8030-97-5, 8031-03-6, 8031-03-6, 8031-03-6, 8031-03-6, 8038-65-1, 8046-19-3, 8046-19-3, 8046-19-3, 8046-19-3, 8046-19-3, 8047-24-3, 8048-51-9, 8048-51-9, 8050-07-5, 8050-07-5, 8050-07-5, 8050-15-5, 8052-14-0, 8052-35-5, 8052-91-3, 8053-33-6, 8053-39-2, 8054-39-5, 8057-49-6, 8057-49-6, 8057-49-6, 8057-49-6, 8057-

49-6, 8060-28-4, 8060-28-4, 8060-28-4, 8060-28-4, 9000-01-5, 9000-03-7, 9000-04-8, 9000-04-8, 9000-04-8, 9000-04-8, 9000-04-8, 9000-05-9, 9000-05-9, 9000-05-9, 9000-05-9, 9000-05-9, 9000-19-5, 9000-19-5, 9000-24-2, 9000-40-2, 9000-40-2, 9000-45-7, 9000-45-7, 9000-55-9, 9000-57-1, 9000-64-0, 9000-64-0, 9000-64-0, 9000-72-0, 9000-72-0, 9000-72-0, 9000-72-0, 9000-75-3, 9000-75-3, 9000-75-3, 9000-78-6, 9000-78-6, 9000-78-6, 9001-05-2, 9005-37-2, 9005-90-7, 9012-37-7, 9014-63-5, 9025-70-1, 9036-66-2, 9050-36-6, 10016-20-3, 10022-28-3, 10022-31-8, 10024-47-2, 10024-56-3, 10024-57-4, 10024-64-3, 10028-22-5, 10030-80-5, 10031-71-7, 10031-82-0, 10031-86-4, 10031-87-5, 10031-88-6, 10031-90-0, 10031-92-2, 10031-93-3, 10031-96-6, 10032-00-5, 10032-02-7, 10032-05-0, 10032-08-3, 10032-11-8, 10032-13-0, 10032-15-2, 10039-39-1, 10042-76-9, 10058-43-2, 10072-05-6, 10094-34-5, 10094-36-7, 10094-40-3, 10094-41-4, 10108-80-2, 10124-43-3, 10138-63-3, 10139-47-6, 10152-76-8, 10152-77-9, 10153-83-0, 10190-99-5, 10192-32-2, 10198-23-9, 10203-28-8, 10208-80-7, 10229-10-4, 10233-13-3, 10235-63-9, 10236-16-5, 10236-47-2, 10255-67-1, 10276-85-4, 10297-72-0, 10316-66-2, 10321-71-8, 10323-20-3, 10326-41-7, 10339-61-4, 10340-23-5, 10352-87-1, 10352-88-2, 10361-37-2, 10361-39-4, 10380-79-7, 10402-33-2, 10402-47-8, 10402-48-9, 10402-52-5, 10411-93-5, 10411-95-7, 10413-18-0, 10414-68-3, 10415-86-8, 10415-87-9, 10415-88-0, 10444-50-5, 10448-26-7, 10458-14-7, 10471-14-4, 10471-96-2, 10482-55-0, 10482-56-1, 10482-65-2, 10482-77-6, 10484-56-7, 10486-14-3, 10486-19-8, 10519-06-9, 10519-17-2, 10519-20-7, 10519-33-2, 10521-91-2, 10521-96-7, 10522-18-6, 10522-33-5, 10522-37-9, 10544-63-5, 10580-25-3, 10588-10-0, 10588-15-5, 10595-82-1, 10599-69-6, 10599-70-9, 10602-34-3, 10606-47-0, 11031-45-1, 11050-62-7, 11113-62-5, 12027-67-7, 12125-02-9, 12135-76-1, 12227-78-0, 12262-03-2, 13002-08-9, 13002-09-0, 13002-11-4, 13019-16-4, 13019-20-0, 13019-22-2, 13049-88-2, 13051-48-4, 13058-12-3, 13100-46-4, 13109-70-1, 13112-63-5, 13112-65-7, 13162-46-4, 13171-00-1, 13175-44-5, 13184-86-6, 13201-46-2, 13215-88-8, 13238-84-1, 13246-52-1, 13254-34-7, 13262-24-3, 13262-27-6, 13269-52-8, 13285-51-3, 13327-56-5, 13341-72-5, 13343-95-8, 13360-64-0, 13360-64-0, 13360-65-1, 13368-65-5, 13398-94-2, 13402-02-3, 13416-74-5, 13419-69-7, 13439-98-0, 13442-89-2, 13442-90-5, 13442-92-7, 13466-78-9, 13473-90-0, 13474-03-8, 13477-00-4, 13481-87-3, 13493-97-5, 13494-06-9, 13494-07-0, 13494-08-1, 13529-27-6, 13532-18-8, 13532-37-1, 13535-43-8, 13548-84-0, 13552-96-0, 13553-09-8, 13562-84-0, 13602-09-0, 13616-82-5, 13623-11-5, 13674-19-6, 13678-58-5, 13678-59-6, 13678-60-9, 13678-61-0, 13678-67-6, 13678-68-7, 13678-69-8, 13678-73-4, 13679-46-4, 13679-60-2, 13679-61-3, 13679-70-4, 13679-72-6, 13679-74-8, 13679-75-9, 13679-83-9, 13679-85-1, 13679-86-2, 13706-86-0, 13708-12-8, 13708-12-8, 13718-94-0, 13720-12-2, 13744-15-5, 13746-66-2, 13748-90-8, 13794-15-5, 13811-71-7, 13828-37-0, 13851-11-1, 13877-91-3, 13877-93-5, 13894-61-6, 13894-62-7, 13894-63-8, 13925-00-3, 13925-03-6, 13925-05-8, 13925-06-9, 13925-07-0, 13925-08-1, 13952-84-6, 13991-37-2, 14027-78-2, 14049-11-7, 14059-92-8, 14062-18-1, 14073-97-3, 14090-87-0, 14109-72-9, 14129-48-7, 14159-61-6, 14173-25-2, 14189-85-6, 14250-95-4, 14252-42-7, 14252-84-7, 14258-49-2, 14259-46-2, 14287-04-8, 14302-13-7, 14309-57-0, 14360-50-0, 14400-67-0, 14414-32-5, 14436-32-9, 14481-52-8, 14481-55-1, 14529-53-4, 14548-46-0, 14576-08-0, 14617-92-6, 14620-52-1, 14667-55-1, 14686-13-6, 14756-03-7, 14765-30-1, 14812-03-4, 14852-31-1, 14882-18-9, 14898-79-4, 14901-07-6, 14914-99-9, 14959-86-5, 14971-14-3, 15111-96-3, 15111-97-4, 15130-76-4, 15186-51-3, 15356-60-2, 15356-74-8, 15399-05-0, 15456-68-5, 15456-70-9, 15469-77-9, 15514-30-0, 15537-55-0, 15570-12-4, 15572-79-9, 15679-09-1, 15679-12-6, 15679-13-7, 15679-19-3, 15706-73-7, 15707-23-0, 15707-24-1, 15707-34-3, 15729-76-7, 15764-04-2, 15764-16-6, 15805-75-1, 15932-80-6, 15986-80-8, 15986-96-6, 15987-00-5, 15991-59-0, 16090-77-0, 16128-68-0, 16215-21-7, 16260-26-7, 16308-92-2, 16356-11-9, 16397-75-4, 16397-78-7, 16400-72-9, 16409-43-1, 16409-45-3, 16409-46-4, 16424-32-1, 16429-21-3, 16436-00-3, 16491-24-0, 16491-25-1, 16491-36-4, 16491-54-6, 16493-80-4, 16509-46-9, 16510-27-3, 16625-69-7, 16630-52-7, 16630-55-0, 16630-60-7, 16630-61-8, 16630-65-2, 16630-66-3, 16635-54-4, 16676-96-3, 16721-38-3, 16721-39-4, 16747-32-3, 16839-97-7, 16930-93-1, 16930-96-4, 16930-97-5, 16930-99-7, 16939-73-4, 16957-70-3, 16958-85-3, 16974-11-1, 17074-02-1, 17102-64-6, 17114-82-8, 17162-29-7, 17194-00-2, 17265-30-4, 17283-81-7, 17369-57-2, 17369-59-4, 17369-60-7, 17369-61-8, 17373-84-1, 17373-89-6, 17373-93-2, 17392-83-5, 17463-01-3, 17465-86-0, 17488-65-2, 17587-33-6, 17600-72-5, 17619-36-2, 17626-75-4, 17627-44-0, 17673-49-3, 17699-16-0, 17909-77-2, 17912-87-7, 17916-91-5, 18031-40-8, 18060-77-0, 18060-79-2, 18114-49-3, 18138-03-9, 18138-04-0, 18138-05-1, 18172-67-3, 18185-81-4, 18189-02-1, 18189-05-4, 18277-27-5, 18294-87-6, 18309-28-9, 18309-32-5, 18318-83-7, 18358-53-7, 18362-97-5, 18368-91-7, 18383-49-8, 18402-82-9, 18409-17-1, 18409-18-2, 18409-20-6, 18409-21-7, 18433-93-7, 18436-37-8, 18449-60-0, 18451-96-2, 18479-49-7, 18479-51-1, 18479-58-8, 18479-68-0, 18492-65-4, 18492-66-5, 18543-68-5, 18640-74-9, 18675-33-7, 18675-35-9, 18679-18-0, 18721-61-4, 18776-92-6, 18794-77-9, 18794-84-8, 18800-53-8, 18824-63-0, 18829-55-5, 18829-56-6, 18836-52-7, 18916-17-1, 18999-28-5, 19009-56-4, 19089-92-0, 19093-20-0, 19141-40-3, 19149-85-0, 19149-86-1, 19162-00-6, 19238-49-4, 19269-28-4, 19317-11-4, 19322-27-1, 19329-89-6, 19342-01-9, 19378-51-9, 19464-94-9, 19473-49-5, 19484-26-5, 19487-61-7, 19549-83-8, 19620-37-2, 19700-21-1, 19773-46-7, 19773-50-3, 19773-56-9, 19780-56-4, 19781-13-6, 19788-49-9, 19788-50-2, 19847-12-2, 19855-52-8, 19872-52-7, 19883-26-2, 19883-27-3, 19883-29-5, 19902-08-0, 19961-52-5, 20013-73-4, 20053-88-7, 20125-81-9, 20125-84-2, 20125-85-3, 20262-26-4, 20273-24-9, 20279-25-8, 20279-43-0, 20279-51-0, 20286-45-7, 20298-71-9, 20298-72-0, 20307-84-0, 20333-39-5, 20347-65-3, 20407-84-5, 20416-08-4, 20425-54-1, 20427-58-1, 20432-40-0, 20474-93-5, 20483-36-7, 20487-40-5, 20489-53-6, 20582-85-8, 20592-10-3, 20662-84-4, 20665-85-4, 20675-95-0, 20680-10-8, 20681-51-0, 20702-77-6, 20748-87-2, 20756-86-9, 20770-40-5, 20777-39-3, 20777-47-3, 20777-49-5, 20780-49-8, 20815-27-4, 20818-81-9, 20859-10-3, 20920-83-6, 20921-04-4, 20996-35-4, 20996-62-7, 21063-71-8, 21129-27-1, 21188-58-9, 21188-60-3, 21188-61-4, 21368-68-3, 21490-63-1, 21593-77-1, 21643-38-9, 21653-20-3, 21662-08-8, 21662-09-9, 21662-13-5, 21662-15-7, 21662-16-8, 21722-83-8, 21834-92-4, 21834-98-0, 21835-01-8, 21862-63-5, 21884-26-4, 21922-58-7, 21944-98-9, 21948-70-9, 21962-24-3, 21963-26-8, 21964-44-3, 22014-48-8, 22026-13-7, 22029-76-1, 22030-19-9, 22047-25-2, 22047-26-3, 22047-27-4, 22072-19-1, 22094-00-4, 22104-78-5, 22104-79-6, 22104-80-9, 22104-81-0, 22319-31-9, 22451-49-6, 22451-50-9, 22610-86-2, 22694-96-8, 22707-35-3, 22771-44-4, 22839-47-0, 22924-15-8, 22940-86-9, 23089-26-1, 23147-57-1, 23267-57-4, 23328-62-3, 23333-91-7, 23433-05-8, 23445-02-5, 23495-12-7, 23511-70-8, 23516-38-3, 23550-40-5, 23556-90-3, 23654-92-4, 23696-85-7, 23726-91-2, 23726-92-3, 23726-93-4, 23726-94-5, 23747-14-0, 23747-34-4, 23747-43-5, 23747-45-7, 23747-48-0, 23769-39-3, 23787-80-6, 23832-18-0, 23986-74-5, 24133-73-1, 24168-70-5, 24202-00-4, 24276-84-4, 24295-03-2, 24317-94-0, 24317-95-1, 24323-24-8, 24323-38-4, 24330-52-7, 24401-36-3, 24415-26-7, 24427-77-8, 24466-84-0, 24653-75-6, 24677-78-9, 24680-50-0, 24683-00-9, 24717-85-9, 24717-86-0, 24720-09-0, 24781-13-3, 24817-51-4, 24851-98-7, 25013-16-5, 25103-58-6, 25152-84-5, 25152-85-6, 25166-87-4, 25226-98-6, 25234-25-7, 25263-97-2, 25265-71-8, 25304-14-7, 25312-34-9, 25322-68-3, 25334-93-4, 25394-57-4, 25395-31-7, 25409-08-9, 25415-62-7, 25415-67-2, 25415-76-3, 25415-84-3, 25524-95-2, 25564-22-1, 25677-40-1, 25680-57-3, 25680-58-4, 25773-40-4, 25790-35-6, 25905-14-0, 25905-16-2, 26001-58-1, 26093-63-0, 26131-91-9, 26153-38-8, 26171-78-8, 26254-92-2, 26266-68-2, 26266-77-3, 26303-90-2, 26370-28-5, 26446-31-1, 26446-32-2, 26450-58-8, 26473-47-2, 26486-13-5, 26486-14-6, 26486-21-5, 26489-01-0, 26494-10-0, 26537-19-9, 26553-46-8, 26553-47-9, 26643-91-4, 26643-92-5, 26651-96-7, 26718-83-2, 26720-19-4, 26850-69-1, 26927-89-9, 26946-66-7, 26946-68-9, 27039-84-5, 27043-05-6, 27113-22-0, 27153-54-4, 27196-00-5, 27215-38-9, 27215-95-8, 27243-08-9, 27300-27-2, 27361-16-6, 27372-03-8, 27538-09-6, 27538-10-9, 27538-35-8, 27539-94-2, 27575-61-7, 27593-23-3, 27625-35-0, 27739-28-2, 27739-29-3, 27743-70-0, 27817-67-0, 27829-72-7, 27871-49-4, 27876-24-0, 27939-60-2, 28024-16-0, 28045-77-4, 28048-94-4, 28060-90-4, 28069-72-9, 28069-74-1, 28079-04-1, 28084-19-7, 28163-84-0, 28217-92-7, 28231-03-0, 28267-32-5, 28290-90-6, 28303-42-6, 28316-62-3, 28324-52-9, 28343-22-8, 28369-24-6, 28376-12-7, 28380-08-7, 28380-12-3, 28467-92-7, 28540-79-6, 28553-12-0, 28588-73-0, 28588-74-1, 28588-75-2, 28588-76-3, 28631-86-9, 28645-51-4, 28664-08-6, 28664-35-9, 28664-35-9, 28672-54-0, 28785-06-0, 28787-36-2, 28801-70-9, 28804-53-7, 28839-13-6, 28880-24-2, 28959-02-6, 29021-36-1, 29066-34-0, 29171-20-8, 29171-21-9, 29210-77-3, 29214-60-6, 29239-07-4, 29350-73-0, 29414-47-9, 29414-56-0, 29460-90-0, 29460-92-2, 29548-14-9, 29548-30-9, 29549-60-8, 29592-92-5, 29592-95-8, 29606-79-9, 29710-33-6, 29714-87-2, 29725-66-4, 29733-18-4, 29759-11-3, 29790-29-2, 29811-50-5, 29895-73-6, 29901-85-7, 29911-28-2, 29926-41-8, 29926-42-9, 29957-43-5, 29990-22-3, 30100-15-3, 30207-98-8, 30304-82-6, 30086-02-3, 30361-28-5, 30361-29-6, 30390-50-2, 30408-61-8, 30418-89-4, 30434-54-9, 30453-31-7, 30460-92-5, 30640-46-1, 30673-36-0, 30673-38-2, 30673-60-0, 30689-75-9, 30895-79-5, 30925-07-6, 30982-35-5, 30982-36-6, 31147-36-1, 31148-31-9, 31195-95-6, 31331-53-0, 31474-57-4, 31499-70-4, 31499-71-5, 31499-72-6, 31501-11-8, 31502-14-4, 31502-19-9, 31539-84-1, 31574-44-4, 31704-80-0, 31835-06-0, 31983-27-4, 32064-72-5, 32074-56-9, 32213-88-0, 32214-88-3, 32214-89-4, 32272-48-3, 32272-57-4, 32349-98-7, 32350-16-6, 32350-16-6, 32388-55-9, 32466-55-0, 32539-85-8, 32637-94-8, 32665-23-9, 32736-91-7, 32737-14-7, 32741-11-0, 32764-98-0, 32844-67-0, 32860-62-1, 32951-19-2, 32953-65-4, 32974-92-8, 33046-81-0, 33049-93-3, 33204-74-9, 33281-91-3, 33368-82-0, 33441-50-8, 33467-73-1, 33467-74-2, 33467-74-2, 33467-76-4, 33467-79-7, 33514-22-6, 33577-16-1, 33603-30-4, 33665-27-9, 33673-62-0, 33673-65-3, 33704-59-5, 33855-57-1, 33880-83-0, 33900-84-4, 33922-80-4, 33959-27-2, 34047-39-7, 34131-99-2, 34135-85-8, 34146-55-9, 34300-94-2, 34316-64-8, 34322-06-0, 34322-09-3, 34362-27-1, 34365-79-2, 34413-34-8, 34413-35-9, 34451-19-9, 34495-71-1, 34545-88-5, 34619-12-0, 34625-23-5, 34686-71-0, 34756-16-6, 34764-02-8, 34884-21-4, 34995-77-2, 35044-63-4, 35044-68-9, 35073-27-9, 35120-10-6, 35148-19-7, 35154-45-1, 35158-25-9, 35178-55-3, 35194-30-0, 35231-44-8, 35234-16-3, 35234-21-0, 35234-22-1, 35234-25-4, 35243-43-7, 35250-53-4, 35274-05-6, 35306-33-3, 35379-09-0, 35416-42-3, 35448-30-7, 35448-31-8, 35472-56-1, 35836-73-8, 35852-42-7, 35852-46-1, 35854-86-5, 35926-04-6, 36203-31-3, 36219-73-5, 36267-71-7, 36431-72-8, 36438-54-7, 36653-82-4, 36701-01-6, 36707-28-5, 36731-41-6, 36781-67-6, 36789-59-0, 36806-46-9, 36809-53-7, 36826-83-2, 36871-78-0, 36880-33-8, 37064-20-3, 37139-85-8, 37160-77-3, 37161-74-3, 37266-93-6, 37526-88-8, 37526-89-9, 37617-03-1, 37645-61-7, 37645-62-8, 37674-63-8, 37811-72-6, 37887-04-0, 37910-77-3, 37918-47-1, 37981-36-5, 37981-37-6, 38028-67-0, 38049-26-2, 38142-45-9, 38183-03-8, 38205-60-6, 38205-64-0, 38237-00-2, 38284-11-6, 38325-25-6, 38360-81-5, 38363-23-4, 38363-29-0, 38376-28-2, 38433-74-8, 38446-21-8, 38462-22-5, 38533-54-9, 38618-23-4, 38713-41-6, 38837-70-6, 38888-81-2, 38917-61-2, 38917-61-2, 38917-62-3, 38917-63-4, 39026-94-3, 39067-80-6, 39156-54-2, 39161-19-8, 39212-23-2, 39251-86-0, 39251-88-2, 39252-02-3, 39252-03-4, 39252-05-6, 39255-32-8, 39556-41-7, 39707-47-6, 39711-79-0, 39736-25-9, 39741-41-8, 39770-05-3, 39800-92-5, 39800-93-6, 39924-27-1, 39924-52-2, 40018-26-6, 40267-72-9, 40348-72-9, 40596-46-1, 40654-82-8, 40709-04-4, 40716-66-3, 40789-98-8, 40790-04-3, 40790-20-3, 40800-76-8, 40853-55-2, 40878-72-6, 40878-73-7, 40923-64-6, 41014-93-1, 41114-00-5, 41199-19-3, 41239-48-9, 41247-05-6, 41270-80-8, 41330-21-6, 41414-75-9, 41453-56-9, 41453-57-0, 41496-43-9, 41496-43-9, 41498-71-9, 41519-18-0, 41519-23-7, 41547-22-2, 41610-76-8, 41653-97-8, 41654-15-3, 41755-67-3, 41803-21-8, 41820-22-8, 41847-86-3, 41903-81-5, 41981-71-9, 41981-72-0, 42075-42-3, 42075-45-6, 42078-65-9, 42125-17-7, 42125-28-0, 42125-30-4, 42125-34-8, 42134-50-9, 42175-41-7, 42231-40-3, 42231-48-1, 42231-74-3, 42231-99-2, 42232-25-7, 42254-63-7, 42348-12-9, 42436-07-7, 42474-44-2, 42598-96-9, 42822-86-6, 42919-64-2, 43039-98-1, 43040-01-3, 43052-87-5, 43108-58-3, 43219-68-7, 45019-28-1, 45206-91-5, 45298-00-8, 49553-64-2, 49576-57-0, 49763-69-1, 49773-24-2, 49776-81-0, 50343-36-7, 50448-95-8, 50623-57-9, 50626-02-3, 50746-09-3, 50746-10-6, 50858-14-5, 50862-12-9, 50888-63-6, 50980-84-2, 50984-52-6, 51100-54-0, 51115-63-0, 51115-64-1, 51115-67-4, 51115-70-9, 51115-77-6, 51117-19-2, 51154-96-2, 51200-86-3, 51210-01-6, 51290-65-4, 51325-37-2, 51352-68-2, 51411-24-6, 51447-08-6, 51532-26-4, 51534-36-2, 51534-66-8, 51608-18-5, 51647-38-2, 51677-68-0, 51685-39-3, 51685-40-6, 51755-66-9, 51755-70-5, 51755-72-7, 51755-83-0, 51755-85-2, 51756-08-2, 51828-97-8, 51856-79-2, 51933-13-2, 52089-55-1, 52363-24-3, 52406-22-1, 52414-91-2, 52513-03-8, 52517-53-0, 52517-54-1, 52558-99-3, 52628-25-8, 52789-73-8, 53046-97-2, 53053-51-3, 53163-97-6, 53184-67-1, 53263-58-4, 53282-12-5, 53398-78-0, 53398-80-4, 53398-81-5, 53398-83-7, 53398-84-8, 53398-85-9, 53398-86-0, 53398-87-1, 53399-81-8, 53405-97-3, 53405-98-4, 53448-07-0, 53451-16-4, 53475-15-3, 53498-30-9, 53498-32-1, 53535-33-4, 53626-94-1, 53651-69-7, 53655-22-4, 53685-77-1, 53751-40-9, 53833-30-0, 53833-32-2, 53833-33-3, 53834-70-1, 53850-34-3, 53850-34-3, 53897-60-2, 53907-46-3, 53939-81-4, 54051-19-3, 54056-51-8, 54300-08-2, 54300-09-3, 54300-10-6, 54306-00-2, 54323-26-1, 54340-72-6, 54355-74-7, 54393-36-1, 54396-97-3, 54410-94-5, 54440-17-4, 54484-66-1, 54484-73-0, 54644-28-9, 54644-28-9, 54653-25-7, 54702-13-5, 54717-12-3, 54717-13-4, 54717-14-5, 54717-17-8, 54723-19-2, 54783-36-7, 54814-64-1, 54815-13-3, 54852-64-1, 54889-48-4, 54934-99-5, 54947-74-9, 54957-02-7, 54982-76-2, 54993-30-5, 55031-15-7, 55050-40-3, 55066-45-0, 55066-56-3, 55145-34-1, 55195-19-2, 55195-23-8, 55249-73-5, 55253-28-6, 55418-52-5, 55505-28-7, 55514-48-2, 55589-62-3, 55704-78-4, 55719-85-2, 55764-22-2, 55764-23-3, 55764-25-5, 55764-28-8, 55910-09-3, 55915-70-3, 56001-43-5, 56011-02-0, 56038-13-2, 56053-84-0, 56134-05-5, 56196-53-3, 56239-91-9, 56269-22-8, 56277-00-0, 56422-50-5, 56423-40-6, 56423-43-9, 56469-39-7, 56554-87-1, 56681-06-2, 56700-78-8, 56747-96-7, 56767-18-1, 56805-23-3, 56816-01-4, 56922-72-6, 56922-73-7, 56922-74-8, 56922-80-6, 56922-81-7, 56922-82-8, 57006-87-8, 57018-53-8, 57069-86-0, 57074-34-7, 57074-35-8, 57074-37-0, 57082-24-3, 57124-87-5, 57129-12-1, 57246-60-3, 57371-42-3, 57378-68-4, 57403-32-4, 57500-00-2, 57568-60-2, 57576-09-7, 57582-42-0, 57582-46-4, 57602-94-5, 57661-23-1, 57675-44-2, 57681-53-5, 57726-26-8, 57743-63-2, 57817-89-7, 57856-81-2, 57893-27-3, 57943-67-6, 57967-68-7, 57967-69-8, 57967-70-1, 57967-71-2, 57967-72-3, 57967-73-4, 57967-74-5, 58031-03-1, 58066-86-7, 58096-46-1, 58102-02-6, 58244-29-4, 58409-60-2, 58430-94-7, 58475-04-0, 58479-55-3, 58543-16-1, 58555-74-1, 58625-95-9, 58809-73-7, 58927-81-4, 58936-30-4, 58985-18-5, 59020-84-7, 59020-85-8, 59020-90-5, 59021-02-2, 59021-03-3, 59021-05-5, 59035-98-2, 59056-71-2, 59184-43-9, 59191-78-5, 59230-57-8, 59259-38-0, 59303-05-8, 59303-07-0, 59303-17-2, 59323-76-1, 59323-81-8, 59324-17-3, 59471-80-6, 59557-05-0, 59558-23-5, 59632-85-8, 59672-05-8, 59726-40-8, 59902-01-1, 60045-26-3, 60045-27-4, 60047-17-8, 60066-88-8, 60160-17-0, 60308-75-0, 60308-76-1, 60329-20-6, 60415-61-4, 60416-24-2, 60437-21-0, 60487-81-2, 60523-21-9, 60642-67-3, 60656-87-3, 60755-05-7, 60770-00-5, 60779-24-0, 60826-15-5, 60899-29-8, 60958-23-8, 60998-24-5, 61041-75-6, 61114-24-7, 61122-71-2, 61197-06-6, 61197-07-7, 61197-09-9, 61295-41-8, 61295-44-1, 61295-50-9, 61295-51-0, 61301-56-2, 61323-24-8, 61389-12-6, 61444-38-0, 61444-39-1, 61444-41-5, 61531-45-1, 61675-72-7, 61683-99-6, 61692-76-0, 61692-79-3, 61692-83-9, 61692-84-0, 61732-96-5, 61758-03-0, 61759-64-6, 61788-89-4, 61789-92-2, 61791-31-9, 61800-40-6, 61810-55-7, 61826-54-8, 61837-77-2, 61889-11-0, 61931-81-5, 61949-23-3, 62028-96-0, 62147-49-3, 62395-45-3, 62439-41-2, 62462-05-9, 62488-24-8, 62488-56-6, 62501-24-0, 62563-80-8, 63012-97-5, 63095-34-1, 63187-91-7, 63196-64-5, 63253-24-7, 63270-14-4, 63302-64-7, 63321-70-0, 63359-63-7, 63408-88-8, 63429-28-7, 63449-64-9, 63449-68-3, 63450-30-6, 63550-99-2, 63697-00-7, 63759-55-7, 63826-25-5, 63885-09-6, 63986-03-8, 64026-45-5, 64187-83-3, 64275-73-6, 64280-32-6, 64461-99-0, 64519-44-4, 64577-91-9, 64677-46-9, 64677-48-1, 64703-98-6, 64741-65-7, 64741-66-8, 64835-96-7, 65114-02-5, 65213-86-7, 65291-43-2, 65330-49-6, 65381-09-1, 65405-67-6, 65405-68-7, 65405-70-1, 65405-76-7, 65405-77-8, 65405-80-3, 65405-84-7, 65416-14-0, 65416-24-2, 65416-28-6, 65423-25-8, 65466-10-6, 65504-45-2, 65504-93-0, 65504-94-1, 65504-95-2, 65504-96-3, 65504-97-4, 65505-16-0, 65505-17-1, 65505-18-2, 65505-24-0, 65505-25-1, 65515-53-9, 65520-45-8, 65530-53-2, 65545-81-5, 65591-12-0, 65620-50-0, 65652-33-7, 65737-52-2, 65813-53-8, 65817-24-5, 65819-74-1, 65887-08-3, 65894-82-8, 65894-83-9, 66161-52-2, 66169-00-4, 66576-71-4, 66634-97-7, 66642-86-2, 66735-69-1, 67024-46-8, 67028-40-4, 67114-38-9, 67121-39-5, 67231-93-0, 67233-91-4, 67234-04-2, 67401-27-8, 67411-27-2, 67452-27-1, 67479-27-0, 67601-05-2, 67633-96-9, 67633-97-0, 67633-99-2, 67634-21-3, 67634-23-5, 67662-96-8, 67663-01-8, 67663-04-1, 67674-36-6, 67674-37-7, 67674-40-2, 67674-41-3, 67689-50-3, 67701-01-3, 67701-02-4, 67701-03-5, 67701-05-7, 67701-06-8, 67701-08-0, 67701-27-3, 67701-30-8, 67701-33-1, 67715-79-1, 67715-80-4, 67715-81-5, 67715-82-6, 67746-25-2, 67746-30-9, 67762-26-9, 67762-36-1, 67762-40-7, 67784-80-9, 67800-85-5, 67801-20-1, 67801-45-0, 67801-65-4, 67845-28-7, 67845-34-5, 67845-45-8, 67845-50-5, 67859-96-5, 67859-99-8, 67860-01-9, 67860-02-0, 67860-38-2, 67874-38-8, 67874-72-0, 67874-76-4, 67874-82-2, 67879-60-1, 67883-77-6, 67883-79-8, 67920-63-2, 67923-58-4, 67936-13-4, 67939-32-6, 67952-39-0, 67952-58-3, 67952-59-4, 67952-60-7, 67952-65-2, 68002-88-0, 68002-94-8, 68039-26-9, 68039-29-2, 68039-33-8, 68039-48-5, 68039-49-6, 68067-33-4, 68081-95-8, 68084-03-7, 68084-07-1, 68113-55-3, 68127-22-0, 68129-81-7, 68132-21-8, 68133-76-6, 68133-78-8, 68133-79-9, 68140-55-6, 68141-15-1, 68141-20-8, 68141-21-9, 68141-22-0, 68141-23-1, 68165-40-2, 68227-51-0, 68227-52-1, 68227-53-2, 68258-95-7, 68298-28-2, 68310-54-3, 68310-59-8, 68310-60-1, 68345-17-5, 68345-22-2, 68366-65-4, 68378-12-1, 68378-13-2, 68391-39-9, 68398-18-5, 68425-08-1, 68443-63-0, 68476-78-8, 68480-16-0, 68480-18-2, 68480-25-1, 68480-26-2, 68480-28-4, 68480-29-5, 68489-09-8, 68489-14-5, 68516-23-4, 68526-83-0, 68527-74-2, 68527-76-4, 68553-81-1, 68553-81-1, 68555-57-7, 68555-58-8, 68555-60-2, 68555-61-3, 68555-63-5, 68555-65-7, 68556-21-8, 68556-22-9, 68602-86-8, 68606-81-5, 68606-81-5, 68606-81-5, 68606-83-7, 68606-83-7, 68606-94-0, 68606-94-0, 68606-97-3, 68606-97-3, 68607-01-2, 68607-01-2, 68608-88-8, 68648-33-9, 68648-39-5, 68650-43-1, 68650-43-1, 68650-43-1, 68650-44-2, 68650-44-2, 68650-44-2, 68650-46-4, 68697-67-6, 68698-58-8, 68698-59-9, 68705-63-5, 68737-61-1, 68739-00-4, 68757-58-4, 68797-67-1, 68797-70-6, 68797-74-0, 68820-35-9, 68855-99-2, 68892-05-7, 68900-67-4, 68915-85-5, 68915-99-1, 68916-02-9, 68916-04-1, 68916-04-1, 68916-04-1, 68916-04-1, 68916-04-1, 68916-05-2, 68916-18-7, 68916-18-7, 68916-19-8, 68916-26-7, 68916-26-7, 68916-26-7, 68916-45-0, 68916-45-0, 68916-46-1, 68916-54-1, 68916-84-7, 68916-84-7, 68916-84-7, 68916-84-7, 68916-84-7, 68916-84-7, 68916-89-2, 68916-91-6, 68916-91-6, 68917-05-5, 68917-11-3, 68917-11-3, 68917-11-3, 68917-13-5, 68917-18-0, 68917-18-0, 68917-18-0, 68917-18-0, 68917-20-4, 68917-46-4, 68917-50-0, 68917-52-2, 68917-52-2, 68917-52-2, 68917-75-9, 68917-78-2, 68919-54-0, 68921-26-6, 68922-06-5, 68922-07-6, 68922-10-1, 68922-11-2, 68937-83-7, 68937-90-6, 68938-58-9, 68952-43-2, 68952-43-2, 68955-98-6, 68956-68-3, 68959-28-4, 68973-20-6, 68990-02-3, 68990-11-4, 68990-14-7, 68990-14-7, 68990-15-8, 68990-15-8, 68990-53-4, 68990-74-9, 68990-74-9, 68991-20-8, 69112-21-6, 69205-08-9, 69275-02-1, 69300-17-0, 69367-40-4, 69382-62-3, 69444-90-2, 69668-87-7, 69834-09-9, 69925-33-3, 70092-44-3, 70158-20-2, 70172-07-5, 70664-96-9, 70786-44-6, 70851-61-5, 70892-20-5, 71011-23-9, 71011-28-4, 71011-28-4, 71011-28-4, 71011-28-4, 71011-28-4, 71048-82-3, 71159-90-5, 71172-26-4, 71172-75-3, 71298-42-5, 71436-87-8, 71500-37-3, 71605-85-1, 71605-86-2, 71605-88-4, 71607-26-6, 71607-53-9, 71617-09-9, 71617-11-3, 71617-12-4, 71648-18-5, 71648-43-6, 71660-03-2, 71662-17-4, 71662-18-5, 71662-27-6, 71662-28-7, 71949-33-2, 71965-26-9, 71978-00-2, 71990-22-2, 72064-62-1, 72109-82-1, 72200-74-9, 72257-53-5, 72258-83-4, 72269-51-3, 72361-41-2, 72437-56-0, 72437-64-0, 72437-68-4, 72724-82-4, 72727-63-0, 72727-70-9, 72779-06-7, 72797-16-1, 72797-17-2, 72845-33-1, 72845-77-3, 72854-42-3, 72869-69-3, 72869-70-6, 72869-75-1, 72881-27-7, 72928-24-6, 72928-33-7, 72928-34-8, 72928-35-9, 72928-36-0, 72928-48-4, 72928-52-0, 72928-53-1, 72934-06-6, 72934-07-7, 72934-16-8, 72939-63-0, 72968-42-4, 72968-47-9, 72968-47-9, 72968-47-9, 72968-47-9, 72968-50-4, 72968-50-4, 72968-50-4, 72968-50-4, 72968-50-4, 72987-57-6, 72987-62-3, 73019-14-4, 73049-51-1, 73049-65-7, 73049-65-7, 73049-65-7, 73049-65-7, 73049-65-7, 73157-43-4, 73296-98-7, 73393-27-8, 73398-85-3, 73435-61-7, 73545-18-3, 73757-27-4, 73952-68-8, 74051-84-6, 74082-06-7, 74094-60-3, 74094-61-4, 74094-62-5, 74094-63-6, 74113-74-9, 74183-60-1, 74298-89-8, 74356-31-3, 74367-97-8, 74525-52-3, 74585-00-5, 74586-09-7, 74595-94-1, 74758-91-1, 74758-93-3, 75039-84-8, 75048-15-6, 75587-05-2, 75587-06-3, 75631-91-3, 75640-26-5, 75853-49-5, 75853-50-8, 75911-79-4, 76238-22-7, 76426-35-2, 76649-14-4, 76649-16-6, 76649-22-4, 76649-23-5, 76649-25-7, 76649-26-8, 76788-46-0, 76917-23-2, 77105-53-4, 77118-93-5, 77129-48-7, 77249-20-8, 77311-02-5, 77341-67-4, 77628-62-7, 77772-06-6, 77772-07-7, 77974-85-7, 78285-90-2, 78417-28-4, 78548-53-5, 78818-78-7, 79925-85-2, 79930-37-3, 80417-97-6, 80638-48-8, 80699-63-4, 80722-28-7, 80866-83-7, 80957-74-0, 81925-81-7, 81974-61-0, 82010-85-3, 82185-41-9, 82654-98-6, 83334-93-4, 83418-53-5, 83418-54-6, 83469-85-6, 83783-78-2, 83783-82-8, 83783-84-0, 83783-86-2, 83861-74-9, 83863-30-3, 84012-12-4, 84012-14-6, 84012-15-7, 84012-15-7, 84012-15-7, 84012-15-7, 84012-15-7, 84012-16-8, 84012-16-8, 84012-20-4, 84012-20-4, 84012-21-5, 84012-22-6, 84012-22-6, 84012-23-7, 84012-23-7, 84012-24-8, 84012-24-8, 84012-24-8, 84012-24-8, 84012-26-0, 84012-26-0, 84012-26-0, 84012-28-2, 84012-30-6, 84012-30-6, 84012-30-6, 84012-33-9, 84012-33-9, 84012-34-0, 84012-34-0, 84012-34-0, 84012-34-0, 84012-35-1, 84012-35-1, 84012-36-2, 84012-36-2, 84012-38-4, 84012-40-8, 84012-40-8, 84012-41-9, 84012-42-0, 84012-43-1, 84012-43-1, 84012-43-1, 84029-91-4, 84082-34-8, 84082-34-8, 84082-34-8, 84082-34-8, 84082-34-8, 84082-36-0, 84082-36-0, 84082-36-0, 84082-36-0, 84082-36-0, 84082-36-0, 84082-36-0, 84082-46-2, 84082-46-2, 84082-54-2, 84082-56-4, 84082-57-5, 84082-58-6, 84082-58-6, 84082-58-6, 84082-60-0, 84082-60-0, 84082-60-0, 84082-60-0, 84082-61-1, 84082-61-1, 84082-61-1, 84082-61-1, 84082-61-1, 84082-61-1, 84082-61-1, 84082-63-3, 84082-63-3, 84082-68-8, 84082-68-8, 84082-68-8, 84082-68-8, 84082-68-8, 84082-68-8, 84082-70-2, 84082-70-2, 84082-70-2, 84082-70-2, 84082-79-1, 84082-79-1, 84082-79-1, 84082-79-1, 84082-81-5, 84082-81-5, 84082-82-6, 84082-82-6, 84082-83-7, 84082-83-7, 84082-83-7, 84110-44-1, 84254-89-7, 84282-44-0, 84434-19-5, 84434-20-8, 84434-23-1, 84434-61-7, 84434-65-1, 84455-19-6, 84455-19-6, 84455-19-6, 84455-29-8, 84455-29-8, 84559-98-8, 84603-56-5, 84603-56-5, 84603-57-6, 84603-58-7, 84603-58-7, 84603-58-7, 84603-60-1, 84603-60-1, 84603-61-2, 84603-62-3, 84603-64-5, 84603-65-6, 84603-65-6, 84603-66-7, 84603-66-7, 84603-66-7, 84603-69-0, 84603-69-0, 84603-69-0, 84603-69-0, 84603-70-3, 84603-73-6, 84604-03-5, 84604-03-5, 84604-07-9, 84604-07-9, 84604-07-9, 84604-09-1, 84604-09-1, 84604-10-4, 84604-11-5, 84604-11-5, 84604-11-5, 84604-12-6, 84604-12-6, 84604-12-6, 84604-12-6, 84604-12-6, 84604-12-6, 84604-13-7, 84604-14-8, 84604-14-8, 84604-14-8, 84604-14-8, 84604-15-9, 84604-17-1, 84604-19-3, 84604-19-3, 84604-20-6, 84604-20-6, 84604-41-1, 84604-42-2, 84604-43-3, 84604-51-3, 84604-52-4, 84604-53-5, 84604-55-7, 84604-59-1, 84623-02-9, 84623-02-9, 84623-02-9, 84625-26-3, 84625-26-3, 84625-27-4, 84625-28-5, 84625-28-5, 84625-29-6, 84625-29-6, 84625-29-6, 84625-29-6, 84625-30-9, 84625-32-1, 84625-35-4, 84625-35-4, 84625-36-5, 84625-36-5, 84625-37-6, 84625-37-6, 84625-39-8, 84625-40-1, 84625-40-1, 84625-40-1, 84625-40-1, 84625-40-1, 84625-40-1, 84625-41-2, 84625-41-2, 84625-42-3, 84625-42-3, 84625-48-9, 84625-48-9, 84625-53-6, 84642-56-8, 84642-58-0, 84642-60-4, 84642-61-5, 84649-79-6, 84649-79-6, 84649-79-6, 84649-81-0, 84649-82-1, 84649-86-5, 84649-86-5, 84649-89-8, 84649-90-1, 84649-92-3, 84649-92-3, 84649-92-3, 84649-93-4, 84649-93-4, 84649-93-4, 84649-96-7, 84649-97-8, 84649-98-9, 84649-98-9, 84649-99-0, 84649-99-0, 84649-99-0, 84649-99-0, 84650-00-0, 84650-00-0, 84650-00-0, 84650-00-0, 84650-00-0, 84650-05-5, 84650-07-7, 84650-07-7, 84650-09-9, 84650-10-2, 84650-10-2, 84650-11-3, 84650-13-5, 84650-13-5, 84650-13-5, 84650-13-5, 84650-15-7, 84650-15-7, 84650-15-7, 84650-18-0, 84650-18-0, 84650-39-5, 84650-40-8, 84650-55-5, 84650-55-5, 84650-59-9, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-63-5, 84650-64-6, 84650-64-6, 84650-66-8, 84681-89-0, 84682-20-2, 84695-94-3, 84695-94-3, 84695-94-3, 84695-95-4, 84695-95-4, 84695-97-6, 84695-99-8, 84696-01-5, 84696-01-5, 84696-03-7, 84696-05-9, 84696-05-9, 84696-05-9, 84696-08-2, 84696-10-6, 84696-11-7, 84696-12-8, 84696-15-1, 84696-15-1, 84696-15-1, 84696-15-1, 84696-17-3, 84696-17-3, 84696-17-3, 84696-19-5, 84696-19-5, 84696-19-5, 84696-20-8, 84696-20-8, 84696-21-9, 84696-21-9, 84696-22-0, 84696-22-0, 84696-23-1, 84696-23-1, 84696-23-1, 84696-24-2, 84696-25-3, 84696-25-3, 84696-25-3, 84696-25-3, 84696-27-5, 84696-40-2, 84696-43-5, 84696-47-9, 84696-47-9, 84696-47-9, 84696-48-0, 84696-50-4, 84696-50-4, 84696-51-5, 84696-51-5, 84696-51-5, 84696-51-5, 84696-51-5, 84696-52-6, 84696-52-6, 84696-53-7, 84696-85-5, 84775-39-3, 84775-39-3, 84775-40-6, 84775-40-6, 84775-41-7, 84775-41-7, 84775-41-7, 84775-41-7, 84775-41-7, 84775-41-7, 84775-41-7, 84775-42-8, 84775-42-8, 84775-44-0, 84775-45-1, 84775-46-2, 84775-46-2, 84775-47-3, 84775-47-3, 84775-47-3, 84775-48-4, 84775-49-5, 84775-50-8, 84775-50-8, 84775-50-8, 84775-50-8, 84775-50-8, 84775-50-8, 84775-50-8, 84775-51-9, 84775-52-0, 84775-52-0, 84775-52-0, 84775-52-0, 84775-55-3, 84775-55-3, 84775-57-5, 84775-60-0, 84775-62-2, 84775-62-2, 84775-62-2, 84775-62-2, 84775-65-5, 84775-66-6, 84775-66-6, 84775-66-6, 84775-66-6, 84775-67-7, 84775-69-9, 84775-70-2, 84775-71-3, 84775-71-3, 84775-71-3, 84775-71-3, 84775-73-5, 84775-74-6, 84775-74-6, 84775-74-6, 84775-74-6, 84775-74-6, 84775-74-6, 84775-74-6, 84775-74-6, 84775-75-7, 84775-77-9, 84775-78-0, 84775-79-1, 84775-81-5, 84775-83-7, 84775-83-7, 84775-89-3, 84775-89-3, 84775-95-1, 84775-95-1, 84775-96-2, 84775-96-2, 84775-97-3, 84775-97-3, 84775-97-3, 84776-05-6, 84776-10-3, 84776-11-4, 84776-23-8, 84776-25-0, 84776-26-1, 84776-27-2, 84776-28-3, 84776-28-3, 84776-63-6, 84776-64-7, 84776-67-0, 84776-68-1, 84776-87-4, 84776-90-9, 84776-98-7, 84776-98-7, 84776-98-7, 84776-98-7, 84776-98-7, 84776-98-7, 84776-98-7, 84787-65-5, 84787-65-5, 84787-66-6, 84787-66-6, 84787-68-8, 84787-68-8, 84787-68-8, 84787-68-8, 84787-68-8, 84787-69-9, 84787-69-9, 84787-70-2, 84787-72-4, 84788-08-9, 84812-71-5, 84812-72-6, 84812-73-7, 84836-94-2, 84836-99-7, 84837-00-3, 84837-06-9, 84837-06-9, 84837-06-9, 84837-06-9, 84837-06-9, 84837-14-9, 84878-24-0, 84878-29-5, 84929-19-1, 84929-19-1, 84929-22-6, 84929-23-7, 84929-27-1, 84929-27-1, 84929-28-2, 84929-28-2, 84929-28-2, 84929-29-3, 84929-29-3, 84929-29-3, 84929-31-7, 84929-31-7, 84929-31-7, 84929-33-9, 84929-34-0, 84929-35-1, 84929-35-1, 84929-35-1, 84929-38-4, 84929-38-4, 84929-41-9, 84929-41-9, 84929-43-1, 84929-43-1, 84929-46-4, 84929-46-4, 84929-47-5, 84929-48-6, 84929-48-6, 84929-51-1, 84929-51-1, 84929-51-1, 84929-52-2, 84929-52-2, 84929-54-4, 84929-54-4, 84929-54-4, 84929-55-5, 84929-61-3, 84929-61-3, 84929-61-3, 84929-61-3, 84929-63-5, 84929-74-8, 84929-74-8, 84929-76-0, 84929-76-0, 84929-76-0, 84929-76-0, 84929-76-0, 84929-76-0, 84929-76-0, 84929-76-0, 84929-78-2, 84929-78-2, 84929-78-2, 84929-78-2, 84929-80-6, 84929-80-6, 84961-44-4, 84961-45-5, 84961-45-5, 84961-45-5, 84961-45-5, 84961-45-5, 84961-45-5, 84961-46-6, 84961-46-6, 84961-46-6, 84961-49-9, 84961-49-9, 84961-49-9, 84961-49-9, 84961-50-2, 84961-50-2, 84961-50-2, 84961-50-2, 84961-50-2, 84961-54-6, 84961-55-7, 84961-56-8, 84961-56-8, 84961-57-9, 84961-57-9, 84961-57-9, 84961-57-9, 84961-57-9, 84961-57-9, 84961-57-9, 84961-58-0, 84961-62-6, 84961-62-6, 84961-66-0, 84961-67-1, 84961-68-2, 84962-67-4, 84988-65-8, 84988-65-8, 84988-66-9, 84988-66-9, 84988-66-9, 84988-74-9, 85005-44-3, 85085-20-7, 85085-20-7, 85085-20-7, 85085-21-8, 85085-25-2, 85085-25-2, 85085-25-2, 85085-26-3, 85085-26-3, 85085-40-1, 85085-43-4, 85085-46-7, 85085-46-7, 85085-51-4, 85085-51-4, 85085-61-6, 85085-62-7, 85085-64-9, 85085-65-0, 85085-69-4, 85085-71-8, 85085-75-2, 85085-76-3, 85085-76-3, 85098-91-5, 85117-06-2, 85117-06-2, 85117-07-3, 85117-07-3, 85117-19-7, 85117-22-2, 85117-22-2, 85136-40-9, 85180-66-1, 85187-05-9, 85187-05-9, 85187-05-9, 85237-83-8, 85248-56-2, 85251-63-4, 85251-63-4, 85251-63-4, 85251-64-5, 85251-67-8, 85391-92-0, 85391-93-1, 85392-03-6, 85392-04-7, 85392-05-8, 85392-06-9, 85407-25-6, 85409-12-7, 85409-36-5, 85410-15-7, 85480-33-7, 85480-37-1, 85480-37-1, 85507-69-3, 85507-69-3, 85508-08-3, 85536-25-0, 85551-27-5, 85554-64-9, 85554-66-1, 85554-69-4, 85554-70-7, 85554-71-8, 85554-72-9, 85586-21-6, 85586-25-0, 85586-66-9, 85586-67-0, 85665-35-6, 85665-90-3, 85699-69-0, 85761-70-2, 85865-69-6, 85909-49-5, 85940-30-3, 85940-31-4, 85940-31-4, 85940-31-4, 85940-32-5, 85940-38-1, 85940-38-1, 85940-38-1, 85960-81-2, 86014-82-6, 86241-90-9, 86290-21-3, 87061-04-9, 87148-01-4, 87148-08-1, 87310-12-1, 87619-90-7, 87891-59-6, 88497-17-0, 88768-45-0, 89534-38-3, 89534-74-7, 89957-39-1, 89957-40-4, 89957-41-5, 89957-42-6, 89957-46-0, 89957-47-1, 89957-48-2, 89957-50-6, 89957-53-9, 89957-53-9, 89957-54-0, 89957-55-1, 89957-56-2, 89957-57-3, 89957-58-4, 89957-59-5, 89957-60-8, 89957-62-0, 89957-62-4, 89957-65-3, 89957-66-4, 89957-67-5, 89957-68-6, 89957-69-7, 89957-73-3, 89957-74-4, 89957-76-6, 89957-77-7, 89957-79-9, 89957-80-2, 89957-82-4, 89957-82-4, 89957-83-5, 89957-84-6, 89957-86-8, 89957-87-9, 89957-88-0, 89957-91-5, 89957-91-5, 89957-91-5, 89957-92-6, 89957-93-7, 89957-97-1, 89957-99-3, 89957-99-3, 89958-08-7, 89958-08-7, 89958-09-8, 89958-09-8, 89958-12-3, 89958-16-7, 89958-17-8, 89958-18-9, 89958-19-0, 89958-20-3, 89958-25-8, 89958-26-9, 89958-28-1, 89958-30-5, 89958-31-6, 89958-33-8, 89997-31-9, 89997-32-0, 89997-33-1, 89997-34-2, 89997-34-2, 89997-34-2, 89997-35-3, 89997-35-3, 89997-35-3, 89997-35-3, 89997-35-3, 89997-35-3, 89997-36-4, 89997-37-5, 89997-38-6, 89997-40-0, 89997-41-1, 89997-43-3, 89997-46-6, 89997-48-8, 89997-49-9, 89997-50-2, 89997-51-3, 89997-53-5, 89997-53-5, 89997-54-6, 89997-55-7, 89997-56-8, 89997-56-8, 89997-56-8, 89997-59-1, 89997-59-1, 89997-59-1, 89997-64-8, 89997-65-9, 89997-65-9, 89997-65-9, 89997-65-9, 89997-65-9, 89997-68-2, 89997-70-6, 89997-71-7, 89997-72-8, 89997-73-9, 89997-73-9, 89997-75-1, 89997-81-9, 89997-82-0, 89997-82-0, 89997-83-1, 89997-84-2, 89997-91-1, 89997-96-6, 89998-01-6, 89998-06-1, 89998-07-2, 89998-08-3, 89998-09-4, 89998-10-7, 89998-11-8, 89998-14-1, 89998-14-1, 89998-14-1, 89998-14-1, 89998-14-1, 89998-16-3, 89998-18-5, 89998-19-6, 89998-20-9, 89998-27-6, 90027-88-6, 90027-90-0, 90027-92-2, 90027-93-3, 90027-94-4, 90027-95-5, 90028-03-8, 90028-03-8, 90028-03-8, 90028-03-8, 90028-03-8, 90028-06-1, 90028-07-2, 90028-09-4, 90028-10-7, 90028-11-8, 90028-11-8, 90028-19-6, 90028-20-9, 90028-20-9, 90028-24-3, 90028-25-4, 90028-33-4, 90028-34-5, 90028-37-8, 90028-39-0, 90028-40-3, 90028-42-5, 90028-43-6, 90028-45-8, 90028-49-2, 90028-50-5, 90028-51-6, 90028-52-7, 90028-52-7, 90028-53-8, 90028-54-9, 90028-55-0, 90028-55-0, 90028-55-0, 90028-56-1, 90028-57-2, 90028-58-3, 90028-61-8, 90028-62-9, 90028-63-0, 90028-64-1, 90028-64-1, 90028-68-5, 90028-69-6, 90028-70-9, 90028-71-0, 90028-72-1, 90028-73-2, 90028-74-3, 90028-74-3, 90028-75-4, 90028-76-5, 90028-80-1, 90028-82-3, 90028-84-5, 90045-20-8, 90045-21-9, 90045-23-1, 90045-25-3, 90045-26-4, 90045-27-5, 90045-28-6, 90045-30-0, 90045-32-2, 90045-33-3, 90045-34-4, 90045-35-5, 90045-36-6, 90045-36-6, 90045-36-6, 90045-38-8, 90045-39-9, 90045-43-5, 90045-43-5, 90045-43-5, 90045-45-7, 90045-45-7, 90045-46-8, 90045-47-9, 90045-47-9, 90045-48-0, 90045-52-6, 90045-56-0, 90045-56-0, 90045-56-0, 90045-57-1, 90045-58-2, 90045-64-0, 90045-65-1, 90045-68-4, 90045-69-5, 90045-70-8, 90045-78-6, 90045-81-1, 90045-81-1, 90045-82-2, 90045-88-8, 90045-89-9, 90045-89-9, 90045-89-9, 90045-90-2, 90045-92-4, 90045-93-5, 90045-93-5, 90045-95-7, 90045-96-8, 90046-01-8, 90046-04-1, 90046-05-2, 90046-10-9, 90046-10-9, 90046-15-4, 90046-16-5, 90046-19-8, 90046-20-1, 90063-37-9, 90063-37-9, 90063-37-9, 90063-37-9, 90063-37-9, 90063-37-9, 90063-37-9, 90063-37-9, 90063-37-9, 90063-40-4, 90063-41-5, 90063-41-5, 90063-42-6, 90063-43-7, 90063-44-8, 90063-46-0, 90063-47-1, 90063-48-2, 90063-52-8, 90063-52-8, 90063-53-9, 90063-54-0, 90063-55-1, 90063-57-3, 90063-60-8, 90063-61-9, 90063-62-0, 90063-64-2, 90063-65-3, 90063-71-1, 90063-71-1, 90063-72-2, 90063-73-3, 90063-76-6, 90063-76-6, 90063-78-8, 90063-79-9, 90063-80-2, 90063-84-6, 90063-85-7, 90063-85-7, 90063-86-8, 90063-86-8, 90063-89-1, 90063-90-4, 90063-95-9, 90063-96-0, 90063-98-2, 90063-99-3, 90063-99-3, 90064-00-9, 90064-04-3, 90064-05-4, 90064-06-5, 90064-06-5, 90064-06-5, 90064-07-6, 90064-07-6, 90064-10-1, 90064-11-2, 90064-13-4, 90064-13-4, 90064-13-4, 90064-15-6, 90064-25-8, 90064-26-9, 90064-27-0, 90064-28-1, 90082-39-6, 90082-43-2, 90082-51-2, 90082-55-6, 90082-58-9, 90082-59-0, 90082-60-3, 90082-60-3, 90082-60-3, 90082-60-3, 90082-60-3, 90082-67-0, 90082-77-2, 90082-81-8, 90082-87-4, 90082-87-4, 90082-98-7, 90083-00-4, 90083-05-9, 90083-05-9, 90083-09-3, 90083-09-3, 90105-89-8, 90105-89-8, 90105-92-3, 90105-94-5, 90105-94-5, 90106-03-9, 90106-05-1, 90106-20-0, 90106-25-5, 90106-25-5, 90106-26-6, 90106-27-7, 90106-27-7, 90106-28-8, 90106-29-9, 90106-30-2, 90106-32-4, 90106-32-4, 90106-34-6, 90106-35-7, 90106-38-0, 90106-38-0, 90106-38-0, 90106-48-2, 90106-49-3, 90106-50-6, 90106-57-3, 90106-59-5, 90106-65-3, 90106-65-3, 90106-67-5, 90106-68-6, 90106-68-6, 90106-82-4, 90106-84-6, 90131-10-5, 90131-10-5, 90131-11-6, 90131-15-0, 90131-21-8, 90131-24-1, 90131-24-1, 90131-24-1, 90131-30-9, 90131-30-9, 90131-34-3, 90131-34-3, 90131-35-4, 90131-36-5, 90131-45-6, 90131-55-8, 90131-55-8, 90131-59-2, 90131-63-8, 90131-63-8, 90131-63-8, 90131-63-8, 90131-63-8, 90131-68-3, 90131-87-6, 90131-88-7, 90131-89-8, 90131-90-1, 90131-98-9, 90131-98-9, 90147-36-7, 90147-36-7, 90147-36-7, 90147-36-7, 90147-36-7, 90147-36-7, 90147-39-0, 90147-43-6, 90147-43-6, 90147-45-8, 90147-49-2, 90147-49-2, 90147-50-5, 90147-51-6, 90147-52-7, 90147-53-8, 90147-55-0, 90147-57-2, 90147-58-3, 90201-28-8, 90244-84-1, 90244-84-1, 90244-84-1, 90244-85-2, 90244-96-5, 90244-99-8, 90244-99-8, 90320-10-8, 90320-12-0, 90320-21-1, 90320-24-4, 90320-25-5, 90320-29-9, 90320-30-2, 90320-31-3, 90320-35-7, 90320-38-0, 90320-39-1, 90320-40-4, 90320-41-5, 90320-42-6, 90320-42-6, 90320-42-6, 90320-43-7, 90320-44-8, 90320-46-0, 90320-47-1, 90320-48-2, 90320-54-0, 90320-56-2, 90397-36-7, 90604-30-1, 90604-47-0, 90604-50-5, 90669-57-1, 90731-56-9, 90879-06-4, 90990-08-2, 90990-15-1, 91031-58-2, 91050-82-7, 91052-03-8, 91052-68-5, 91052-69-6, 91052-70-9, 91052-71-0, 91052-72-1, 91052-73-2, 91052-92-5, 91082-91-6, 91418-25-6, 91697-20-0, 91697-21-1, 91697-22-2, 91697-92-6, 91697-93-7, 91721-63-0, 91721-63-0, 91721-69-6, 91721-70-9, 91721-71-0, 91721-72-1, 91721-76-5, 91722-19-9, 91722-21-3, 91722-21-3, 91722-22-4, 91722-29-1, 91722-39-3, 91722-47-3, 91722-47-3, 91722-58-6, 91722-58-6, 91722-58-6, 91722-69-9, 91722-81-5, 91723-39-6, 91723-41-0, 91723-45-4, 91723-46-5, 91723-51-2, 91723-52-3, 91745-07-2, 91745-12-9, 91745-20-9, 91745-21-0, 91745-63-0, 91745-64-1, 91745-65-2, 91745-71-0, 91745-71-0, 91745-71-0, 91745-71-0, 91745-73-2, 91745-82-3, 91745-88-9, 91745-90-3, 91745-92-5, 91745-99-2, 91746-00-8, 91746-01-9, 91746-02-0, 91770-08-0, 91770-12-6, 91770-12-6, 91770-14-8, 91770-14-8, 91770-17-8, 91770-18-2, 91770-19-3, 91770-20-6, 91770-21-7, 91770-22-8, 91770-23-9, 91770-23-9, 91770-24-0, 91770-38-6, 91770-47-7, 91770-48-8, 91770-48-8, 91770-48-8, 91770-51-3, 91770-75-1, 91770-81-9, 91770-83-1, 91770-83-1, 91770-88-6, 91770-88-6, 91770-91-1, 91770-92-2, 91771-22-1, 91771-23-2, 91771-24-3, 91771-25-4, 91771-26-5, 91771-34-5, 91771-36-7, 91771-41-4, 91771-46-9, 91771-46-9, 91771-49-2, 91771-50-5, 91771-50-5, 91771-51-6, 91771-51-6, 91771-53-8, 91771-55-0, 91771-56-1, 91771-57-2, 91771-63-0, 91771-66-3, 91771-67-4, 91771-69-6, 91771-73-2, 91844-82-5, 91844-87-0, 91844-88-1, 91844-92-7, 91844-92-7, 91844-94-9, 91845-25-9, 91845-35-1, 91845-35-1, 91845-35-1, 91845-35-1, 91845-48-6, 91845-48-6, 91845-53-3, 91845-58-8, 91845-60-2, 91845-61-3, 91845-63-5, 91845-64-6, 91845-65-7, 92015-65-1, 92112-69-1, 92113-05-8, 92113-07-0, 92113-09-2, 92113-34-3, 92113-39-8, 92128-82-0, 92128-83-1, 92128-84-2, 92128-86-4, 92129-38-9, 92129-98-1, 92201-14-4, 92201-43-9, 92201-44-0, 92201-45-1, 92201-47-3, 92201-48-4, 92201-49-5, 92201-56-4, 92201-56-4, 92201-57-5, 92201-62-2, 92201-63-3, 92201-65-5, 92201-65-5, 92201-66-6, 92201-66-6, 92201-79-1, 92201-80-4, 92201-90-6, 92201-95-1, 92201-96-2, 92202-04-5, 92202-24-9, 92202-24-9, 92202-24-9, 92202-45-4, 92202-48-7, 92332-31-5, 92332-31-5, 92332-32-6, 92346-82-2, 92346-83-3, 92346-86-6, 92346-87-7, 92346-94-6, 92346-96-8, 92346-97-9, 92346-97-9, 92346-98-0, 92346-99-1, 92347-00-7, 92347-01-8, 92347-11-0, 92347-12-1, 92347-13-2, 92347-21-2, 92347-32-5, 92372-05-9, 92456-63-8, 92456-63-8, 92456-66-1, 92456-66-1, 92456-66-1, 92456-67-2, 92456-68-3, 92456-69-4, 92456-74-1, 92456-82-1, 92456-82-1, 92456-83-2, 92456-84-3, 92456-85-4, 92456-85-4, 92456-99-0, 92457-09-5, 92457-10-8, 92457-18-6, 92457-26-6, 92457-39-1, 92457-45-9, 92457-49-3, 92457-50-6, 92502-62-0, 92502-65-3, 92502-66-4, 92585-08-5, 92623-74-0, 92623-76-2, 92704-00-2, 92704-06-8, 92704-37-5, 92729-55-0, 92797-27-8, 92797-36-9, 92874-96-9, 92874-98-1, 92875-00-8, 92875-04-2, 92875-05-3, 92875-06-4, 92900-67-9, 93002-38-1, 93028-58-1, 93062-61-4, 93062-66-9, 93062-71-6, 93062-76-1, 93062-85-2, 93164-83-1, 93164-87-5, 93164-88-6, 93164-89-7, 93164-91-1, 93164-92-2, 93164-93-3, 93164-97-7, 93165-01-6, 93165-03-8, 93165-11-8, 93165-11-8, 93165-17-4, 93165-23-2, 93165-39-0, 93165-40-3, 93165-40-3, 93165-41-4, 93165-42-5, 93165-51-6, 93165-51-6, 93165-53-8, 93165-54-9, 93165-64-1, 93165-66-3, 93165-66-3, 93165-81-2, 93165-81-2, 93165-81-2, 93165-81-2, 93165-81-2, 93165-86-7, 93333-75-6, 93333-76-7, 93333-77-8, 93333-81-4, 93333-84-7, 93333-87-0, 93333-94-9, 93334-29-3, 93334-37-3, 93334-43-1, 93334-48-6, 93347-97-3, 93348-00-6, 93348-01-7, 93348-06-2, 93348-07-3, 93348-13-1, 93348-14-2, 93348-17-5, 93348-35-7, 93348-48-2, 93348-59-5, 93348-65-3, 93348-66-4, 93384-25-9, 93384-28-2, 93384-28-2, 93455-69-7, 93455-73-3, 93455-75-5, 93455-95-9, 93571-82-5, 93572-53-3, 93685-34-8, 93685-35-9, 93685-36-0, 93685-44-0, 93685-45-1, 93685-46-2, 93685-55-3, 93685-61-1, 93685-62-2, 93685-89-3, 93685-89-3, 93685-93-9, 93685-94-0, 93685-95-1, 93685-96-2, 93685-96-2, 93686-22-7, 93686-22-7, 93762-24-4, 93762-34-6, 93762-35-7, 93763-03-2, 93763-95-2, 93777-70-9, 93804-64-9, 93805-23-3, 93805-35-7, 93805-72-2, 93839-05-5, 93843-29-9, 93859-17-7, 93859-18-8, 93859-19-9, 93892-06-9, 93892-09-2, 93893-91-5, 93904-38-2, 93905-03-4, 93917-74-9, 93919-00-7, 93919-04-1, 93919-13-2, 93919-89-2, 93940-61-5, 93951-35-0, 93963-11-2, 93964-77-3, 93980-90-6, 94021-39-3, 94021-42-8, 94021-43-9, 94021-78-0, 94021-96-2, 94021-97-3, 94022-04-5, 94022-06-7, 94022-07-8, 94022-32-9, 94022-33-0, 94071-12-2, 94087-24-8, 94087-83-9, 94087-84-0, 94088-12-7, 94088-27-4, 94088-33-2, 94088-34-3, 94089-01-7, 94089-02-8, 94089-21-1, 94089-22-2, 94089-23-3, 94094-62-9, 94109-50-9, 94109-96-3, 94109-97-4, 94109-98-5, 94109-99-6, 94133-43-4, 94133-55-8, 94133-57-0, 94133-92-3, 94134-03-9, 94135-08-7, 94159-29-2, 94159-31-6, 94159-32-7, 94166-89-9, 94166-90-2, 94166-92-4, 94166-97-9, 94166-98-0, 94166-99-1, 94167-00-7, 94167-13-2, 94167-14-3, 94200-09-6, 94200-10-9, 94200-13-2, 94201-34-0, 94201-63-5, 94201-64-6, 94201-69-1, 94202-15-0, 94231-50-2, 94247-15-1, 94248-13-2, 94265-97-1, 94265-98-2, 94265-99-3, 94266-47-4, 94266-47-4, 94278-21-4, 94278-25-8, 94278-26-9, 94278-27-0, 94279-61-5, 94279-66-0, 94279-68-2, 94279-77-3, 94279-78-4, 94279-80-8, 94279-84-2, 94279-87-5, 94279-95-5, 94279-95-5, 94279-99-9, 94280-14-5, 94280-15-6, 94293-57-9, 94333-66-1, 94333-92-3, 94333-93-4, 94334-00-6, 94334-04-0, 94334-09-5, 94334-32-4, 94349-62-9, 94349-64-1, 94349-69-6, 94349-73-2, 94349-79-8, 94349-81-2, 94349-81-2, 94349-81-2, 94349-81-2, 94349-85-6, 94386-39-7, 94441-99-3, 94465-73-3, 94465-75-5, 94465-81-3, 94581-24-5, 94624-07-4, 94891-17-5, 94891-18-6, 94891-21-1, 94891-22-2, 94891-23-3, 94891-24-4, 94891-27-7, 94891-27-7, 94891-27-7, 94891-27-7, 94891-28-8, 94891-28-8, 94918-97-5, 94944-89-5, 95008-94-9, 95008-95-0, 95193-53-6, 95193-64-9, 95193-67-2, 95193-68-3, 95371-14-5, 96097-18-6, 96690-56-1, 96690-56-1, 96690-56-1, 96690-56-1, 96690-58-3, 97158-38-8, 97231-35-1, 97281-12-4, 97281-14-6, 97281-15-7, 97281-16-8, 97281-35-1, 97281-42-0, 97281-42-0, 97281-43-1, 97281-55-5, 97404-53-0, 97404-53-0, 97404-53-0, 97404-53-0, 97416-87-0, 97435-00-2, 97435-01-3, 97435-04-6, 97435-05-7, 97435-07-9, 97435-08-0, 97435-09-1, 97435-11-5, 97435-12-6, 97435-13-7, 97435-15-9, 97435-16-0, 97489-11-7, 97552-89-1, 97552-97-1, 97552-98-2, 97553-30-5, 97553-37-2, 97553-38-3, 97553-47-4, 97553-54-3, 97553-55-4, 97553-56-5, 97553-57-6, 97553-58-7, 97593-05-0, 97593-06-1, 97593-13-0, 97593-13-0, 97593-20-9, 97593-29-8, 97593-40-3, 97593-52-7, 97593-54-9, 97615-82-2, 97659-49-9, 97659-61-5, 97659-63-7, 97659-64-8, 97659-68-2, 97659-71-7, 97659-89-7, 97660-19-0, 97675-51-9, 97675-52-0, 97675-52-0, 97675-56-4, 97675-57-5, 97675-59-7, 97675-70-2, 97675-73-5, 97675-74-6, 97675-74-6, 97675-74-6, 97675-75-7, 97675-76-8, 97675-78-0, 97675-82-6, 97675-83-7, 97675-84-8, 97675-98-4, 97676-10-3, 97676-13-6, 97676-13-6, 97676-19-2, 97676-22-7, 97676-22-7, 97676-22-7, 97692-56-3, 97721-86-3, 97721-87-4, 97721-89-6, 97721-90-9, 97721-91-0, 97721-92-1, 97721-93-2, 97721-94-3, 97721-95-4, 97722-03-7, 97722-20-8, 97722-26-4, 97765-54-3, 97765-56-5, 97765-57-6, 97765-60-1, 97765-61-2, 97765-62-3, 97765-72-5, 97765-73-6, 97765-80-5, 97766-24-0, 97766-30-8, 97844-16-1, 97861-82-0, 97866-86-9, 97890-13-6, 97926-09-5, 97926-16-4, 97926-17-5, 97926-23-3, 97926-27-7, 97926-28-8, 97926-32-4, 97926-33-5, 97926-42-6, 97926-65-3, 97926-66-4, 97927-03-2, 97927-04-3, 97927-05-4, 97927-06-5, 97952-48-2, 97952-49-3, 97952-52-8, 97952-53-9, 97952-54-0, 97952-55-1, 97952-56-2, 97952-57-3, 97952-59-5, 97952-62-0, 97952-71-1, 98072-02-7, 98084-79-8, 98143-59-0, 98143-62-5, 98143-66-9, 98143-67-0, 98143-69-2, 98143-70-5, 98306-00-4, 98306-01-5, 98314-98-8, 98395-72-3, 98395-73-4, 98395-74-5, 98561-44-5, 98653-80-6, 98653-85-1, 98653-86-2, 98654-08-1, 98654-09-2, 99253-91-5, 99583-29-6, 99910-84-6, 100084-89-7, 100084-89-7, 100084-89-7, 100084-89-7, 100084-96-6, 100085-39-0, 100085-51-6, 100209-22-1, 100209-23-2, 100209-41-4, 100209-50-5, 100298-73-5, 100299-04-5, 100403-14-3, 100403-17-6, 100403-60-9, 100573-91-9, 100743-68-8, 101417-25-8, 101426-31-7, 101517-87-7, 101780-73-8, 101853-47-8, 102242-62-6, 102322-83-8, 102369-06-2, 103798-68-1, 103798-69-2, 103798-70-5, 104228-51-5, 104691-40-9, 104691-41-0, 108499-33-8, 108766-16-1, 109537-55-5, 110823-66-0, 113486-29-6, 114099-96-6, 115422-59-8, 115869-76-6, 116505-60-3, 116963-97-4, 117013-33-9, 118869-62-8, 121199-28-8, 121432-33-5, 121746-18-7, 122334-93-4, 122384-75-2, 122397-96-0, 122861-78-3, 127248-84-4, 127931-21-9, 128331-45-3, 128331-48-6, 128331-49-7, 129316-65-0, 129319-15-9, 129828-29-1, 132940-73-9, 133447-37-7, 133860-42-1, 134359-15-2, 134454-31-2, 136115-65-6, 136115-66-7, 136954-20-6, 136954-21-7, 136954-22-8, 136954-25-1, 137443-18-6, 139564-42-4, 139564-43-5, 139693-24-6, 142896-09-1, 142896-11-5, 142896-12-6, 143764-28-7, 150436-68-3, 150767-88-7, 153175-57-6, 155639-75-1, 156324-78-6, 156324-82-2, 156420-69-8, 156472-94-5, 156679-39-9, 159113-17-4, 163038-04-8, 163038-04-8, 163266-17-9, 164524-93-0, 165191-91-3, 169054-69-7, 170678-49-6, 172201-58-0, 180031-78-1, 180348-60-1, 180964-47-0, 183815-52-3, 188417-26-7, 188590-62-7, 195863-84-4, 196109-18-9, 197098-61-6, 198404-98-7, 202188-43-0, 202188-46-3, 203719-53-3, 203719-54-4, 207801-32-9, 207983-28-6, 211241-68-8, 211323-05-6, 214220-85-6, 220621-22-7, 223748-34-3, 227456-27-1, 227456-28-2, 227456-33-9, 233665-90-2, 233665-91-3, 233665-96-8, 233665-98-0, 233666-03-0, 233666-04-1, 233666-09-6, 238757-27-2, 238757-30-7, 238757-35-2, 238757-42-1, 238757-63-6, 238757-65-8, 238757-71-6, 246166-03-0, 246511-74-0, 252736-36-0, 252736-39-3, 252736-40-6, 252736-41-7, 253596-70-2, 253596-99-5, 253679-74-2, 258823-39-1, 308065-15-8, 308068-42-0, 324742-96-3, 333384-99-9, 376595-42-5, 400052-49-5, 406179-71-3, 406700-80-9, 437770-28-0, 444085-42-1, 462631-45-4, 479547-57-4, 544409-58-7, 544714-08-1, 548774-80-7, 563187-91-7, 608514-55-2, 608514-56-3, 612071-27-9, 648434-55-3, 686298-93-1, 697290-76-9, 714229-20-6, 723759-62-4, 744251-93-2, 745047-51-2, 745047-53-4, 745047-94-3, 745047-97-6, 781674-18-8, 782498-03-7, 791807-20-0, 792933-14-3, 796857-79-9, 827024-53-3, 831213-72-0, 847565-09-7, 850309-45-4, 851768-51-9, 851768-52-0, 852379-28-3, 852997-28-5, 852997-30-9, 853947-36-1, 853947-47-4, 871465-49-5, 876748-60-6, 879496-95-4, 883215-02-9, 888021-82-7, 891781-90-1, 896447-13-5, 896447-14-6, 897630-96-5, 906079-63-8, 915971-43-6, 917750-72-2, 923291-29-6, 923593-56-0, 923593-57-1, 929116-08-5, 929222-96-8, 930587-76-1, 955371-64-9, 957136-80-0, 958660-02-1, 958660-04-3, 977000-16-0, 977000-66-0, 977000-82-0, 977001-13-0, 977001-38-9, 977001-63-0, 977001-82-3, 977001-93-6, 977002-36-0, 977002-44-0, 977002-61-1, 977004-06-0, 977004-06-0, 977004-06-0, 977005-95-0, 977005-95-0, 977007-65-0, 977007-72-9, 977007-75-2, 977007-79-6, 977007-81-0, 977007-81-0, 977007-85-4, 977017-81-4, 977017-82-5, 977017-84-7, 977018-19-1, 977018-21-5, 977018-53-3, 977023-22-5, 977029-66-5, 977029-68-7, 977029-75-6, 977029-76-7, 977038-75-7, 977038-80-4, 977038-85-9, 977038-86-0, 977048-47-7, 977050-15-9, 977050-15-9, 977050-60-4, 977050-87-5, 977051-01-6, 977051-14-1, 977051-22-1, 977051-23-2, 977051-39-0, 977051-58-3, 977051-63-0, 977051-72-1, 977051-88-9, 977051-90-3, 977051-94-7, 977051-98-1, 977051-99-2, 977052-03-1, 977052-16-6, 977052-32-6, 977052-36-0, 977052-44-0, 977052-57-5, 977052-73-5, 977052-81-5, 977052-82-6, 977060-66-4, 977075-23-2, 977075-23-2, 977082-99-7, 977083-24-1, 977088-38-2, 977089-41-0, 977090-74-6, 977090-74-6, 977090-78-0, 977091-24-9, 977091-83-0, 977103-80-2, 977138-70-7, 977155-29-5, 977184-01-2, 977185-29-7, 977187-65-7, 984650-63-5, 1003050-32-5, 1006684-20-3, 1033366-59-4, 1048028-77-8, 1048028-77-8, 1064678-08-5, 1093200-92-0, 1094004-39-3, 1119711-29-3, 1119831-25-2, 1120363-98-5, 1123751-39-2, 1186004-10-3, 1190229-37-8, 1190230-47-7, 1192738-48-9, 1197991-17-5, 1217341-48-4, 1256932-15-6, 52-51-7, 56-23-5, 56-35-9, 56-69-9, 68-12-2, 71-48-7, 74-31-7, 75-91-2, 77-58-7, 79-07-2, 79-74-3, 80-15-9, 80-30-8, 80-43-3, 83-46-5, 83-48-7, 84-61-7, 84-69-5, 84-74-2, 84-78-6, 85-60-9, 85-68-7, 85-70-1, 87-18-3, 88-04-0, 89-19-0, 97-23-4, 98-29-3, 99-20-7, 104-68-7, 105-76-0, 106-12-7, 109-89-7, 110-22-5, 111-66-0, 112-85-6, 117-39-5, 117-81-7, 117-83-9, 120-55-8, 120-78-5, 121-54-0, 123-42-2, 123-99-9, 126-99-8, 139-12-8, 140-04-5, 141-20-8, 143-28-2, 151-13-3, 461-58-5, 474-62-4, 474-67-9, 475-31-0, 540-59-0, 543-80-6, 627-75-8, 636-61-3, 991-84-4, 1135-24-6, 1302-78-9, 1304-29-6, 1312-76-1, 1333-86-4, 1762-95-4, 3064-70-8, 3238-40-2, 3634-83-1, 3720-97-6, 4080-31-3, 4196-89-8, 4618-18-2, 4744-47-2, 5012-62-4, 7446-70-0, 7585-39-9, 7632-50-0, 7705-08-0, 7727-43-7, 7773-06-0, 7783-18-8, 7785-84-4, 7785-87-7, 8001-75-0, 8001-76-1, 8002-26-4, 8002-80-0, 8008-74-0, 8020-84-6, 8029-34-3, 8029-81-0, 8030-76-0, 8049-98-7, 8060-28-4, 9000-01-5, 9000-40-2, 9006-50-2, 9007-28-7, 9007-83-4, 9007-90-3, 9010-10-0, 9025-57-4, 9036-66-2, 9050-36-6, 10016-20-3, 10124-37-5, 10193-36-9, 10380-28-6, 11132-73-3, 12003-49-5, 12167-74-7, 12168-85-3, 13765-36-1, 14986-84-6, 16715-59-6, 17540-75-9, 20018-09-1, 25168-73-4, 25339-99-5, 26444-49-5, 26761-40-0, 26762-93-6, 27554-26-3, 32687-78-8, 34612-38-9, 35691-65-7, 51229-78-8, 57569-40-1, 65072-00-6, 66071-94-1, 68458-87-7, 68515-50-4, 68525-86-0, 68607-88-5, 68650-43-1, 68990-53-4, 68990-74-9, 68991-43-5, 70983-55-0, 72968-47-9, 72968-50-4, 84012-14-6, 84012-18-0, 84012-24-8, 84012-26-0, 84012-26-0, 84012-26-0, 84012-26-0, 84012-26-0, 84012-26-0, 84012-33-9, 84012-43-1, 84012-44-2, 84012-44-2, 84082-34-8, 84082-55-3, 84082-55-3, 84082-57-5, 84195-49-3, 84603-58-7, 84603-58-7, 84604-16-0, 84625-29-6, 84625-34-3, 84649-82-1, 84649-98-9, 84650-00-0, 84650-15-7, 84650-16-8, 84650-55-5, 84650-60-2, 84650-60-2, 84650-60-2, 84650-60-2, 84650-60-2, 84775-55-3, 84775-71-3, 84775-94-0, 84776-66-9, 84776-66-9, 84776-66-9, 84776-66-9, 84776-

66-9, 84776-66-9, 84929-43-1, 84929-61-3, 84929-61-3, 84929-61-3, 84961-57-9, 89957-89-1, 89957-89-1, 89957-90-4, 89957-90-4, 89997-35-3, 89997-82-0, 89998-03-8, 89998-03-8, 89998-03-8, 89998-03-8, 89998-03-8, 89998-03-8, 89998-03-8, 89998-14-1, 89998-14-1, 90028-20-9, 90028-42-5, 90045-43-5, 90045-97-9, 90045-97-9, 90045-97-9, 90045-97-9, 90063-52-8, 90063-86-8, 90082-41-0, 90082-81-8, 90106-39-1, 90131-10-5, 90131-25-2, 90131-25-2, 90131-25-2, 90131-34-3, 90131-63-8, 90131-63-8, 90320-37-9, 91722-47-3, 91744-32-0, 91745-12-9, 91770-12-6, 91770-24-0, 91770-48-8, 92202-24-9, 93165-81-2, 93384-22-6, 93384-40-8, 94349-91-4, 97593-13-0, 97676-13-6, 98143-70-5, 100684-25-1, 102242-62-6.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of releasing an edible material into an environment, comprising loading into a system for releasing an edible material a plurality of capsules, each containing therein an edible material, and activating the system to dispense a fluid obtained from edible materials contained in at least one of said capsules;
    wherein said loading comprises loading at least one capsule that contains therein a taste-modifying substance, and wherein said system comprises:
    a plurality of compartments adapted to receive said plurality of capsules;
    a dispenser system configured for dispensing into an environment a fluid obtained from at least one edible material; and
    a controller configured for receiving data pertaining to a selection of at least two of said compartments and for signaling said dispenser system to dispense fluids obtained from edible materials contained in capsules of said selected compartments.

2. The method according to claim 1, wherein said loading comprises loading at least two capsules that contain therein a different edible material.

3. The method according to claim 1, wherein said loading comprises loading at least two capsules that contain the same edible material but at a different concentration.

4. The method according to claim 1, wherein said dispenser system comprises a plurality of dispensing elements and wherein said controller signals each dispensing element to dispense a fluid obtained from an edible material contained in a different capsule.

5. The method according to claim 1, wherein said dispenser system comprises at least one fluid channel forming fluid communication between a respective compartment and said environment, wherein said controller is configured for opening and blocking said at least one fluid channel, thereby to establish or prevent said fluid communication.

6. The method according to claim 1, wherein said system comprises a mixing chamber, wherein said dispenser system comprises at least one fluid channel forming fluid communication between a respective compartment and said mixing chamber, and wherein said controller is configured for opening and blocking said at least one fluid channel, thereby to establish or prevent said fluid communication.

7. The method according to claim 1, wherein said controller is configured for receiving data pertaining to a mixing ratio, and to control amounts of said fluids responsively to said mixing ratio.

8. The method according to claim 7, wherein said system comprises a weight measuring device constituted to measure a weight of each capsule separately, wherein said controller is configured for receiving weight data from said weight measuring device and to control said amounts based on said weight data.

9. The method according to claim 8, wherein said system comprises a user interface configured for entering said mixing ratio.

10. The method according to claim 7, wherein said system comprises a user interface configured for entering said mixing ratio.

11. The method according to claim 1, wherein said system comprises a weight measuring device constituted to measure a weight of each capsule separately.

12. The method according to claim 1, wherein said system comprises a user interface configured for at least one of (i) activating said controller and/or said dispenser system, (ii) deactivating said controller and/or said dispenser system, and (iii) entering said selection data.

13. The method according to claim 1, wherein said system comprises a communication system configured for communicating with a remote user interface.

14. The method according to claim 1, wherein said dispenser system is configured for heating said edible material to form said fluid.

15. The method of claim 14, wherein said heating is by a flame or by resistive heater.

16. The method according to claim 1, wherein said dispenser system is configured to apply ultrasound waves to said edible material thereby to dispense said fluid.

17. The method according to claim 1, wherein said dispenser system is configured to apply a stream of gas to said edible material thereby to dispense said fluid.

18. The method according to claim 1, wherein said dispenser system comprises at least one of an atomizer, a humidifier, a blower and a fan.

19. The method according to claim 1, wherein at least one of said capsules contains said edible material in a solid state as room temperature.

20. The method according to claim 1, wherein at least one of said capsules contains said edible material in a liquid state as room temperature.

21. A method of releasing an edible material into an environment, comprising loading into a system for releasing an edible material a plurality of capsules, each containing therein an edible material, and activating the system to dispense a fluid obtained from edible materials contained in at least one of said capsules;

wherein said loading comprises loading at least one capsule that contains therein a taste-modifying substance, and wherein said system comprises:

a plurality of compartments adapted to receive said plurality of capsules;

a weight measuring device constituted to measure a weight of each capsule separately;

a dispenser system configured for dispensing into an environment a fluid obtained from at least one edible material; and a controller configured for receiving data pertaining to a selection of at least two of said compartments and for signaling said dispenser system to dispense fluids obtained from edible materials contained in capsules of said selected compartments.

22. The method according to claim 21, wherein said controller is configured for receiving data pertaining to a mixing ratio, and to control amounts of said fluids responsively to said mixing ratio.

23. The method according to claim 22, wherein said controller is configured for receiving weight data from said weight measuring device and to control said amounts based on said weight data.

* * * * *